United States Patent
Peterson

(10) Patent No.: US 9,701,715 B2
(45) Date of Patent: Jul. 11, 2017

(54) CONFORMATIONALLY-CONSTRAINED KINKED ENDOSOMAL-DISRUPTING PEPTIDES

(71) Applicant: THE UNIVERSITY OF KANSAS, Lawrence, KS (US)

(72) Inventor: Blake R. Peterson, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 14/438,194

(22) PCT Filed: Oct. 3, 2013

(86) PCT No.: PCT/US2013/063250
§ 371 (c)(1),
(2) Date: Apr. 23, 2015

(87) PCT Pub. No.: WO2014/055754
PCT Pub. Date: Apr. 10, 2014

(65) Prior Publication Data
US 2015/0274780 A1 Oct. 1, 2015

Related U.S. Application Data

(60) Provisional application No. 61/710,289, filed on Oct. 5, 2012.

(51) Int. Cl.
*A61K 38/02* (2006.01)
*C07K 7/08* (2006.01)
(Continued)

(52) U.S. Cl.
CPC ............... *C07K 7/08* (2013.01); *A61K 38/10* (2013.01); *A61K 47/42* (2013.01);
(Continued)

(58) Field of Classification Search
None
See application file for complete search history.

(56) References Cited

U.S. PATENT DOCUMENTS 6,825,319 B1 * 11/2004 Blank .................. C07K 14/775
424/185.1
2006/0229235 A1 10/2006 Peterson
(Continued)

FOREIGN PATENT DOCUMENTS

| CA | 1340656 | * | 7/1999 | ............... C07K 7/06 |
| WO | WO 2006052723 A2 | * | 5/2006 | ........... C07K 14/723 |
| WO | WO2011019942 A2 | * | 2/2011 | ........... C07K 31/575 |

OTHER PUBLICATIONS

Sun et al. Selective Disruption of Early/Recycling Endosomes: Release of Disulfide-Linked Cargo Mediated by a N—Alkyl-3β-Cholesterylamine-Capped Peptide. J Am Chem Soc. Aug. 6, 2008; 130(31): 10064-10065.*
(Continued)

*Primary Examiner* — Satyanarayana R Gudibande
*Assistant Examiner* — Jia-Hai Lee
(74) *Attorney, Agent, or Firm* — Maschoff Brennan

(57) ABSTRACT

A conformationally-constrained kinked peptide includes: a conformationally-constraining portion and a kinked portion linked to the conformationally-constraining portion that conformationally constrains the kinked portion, the kinked portion comprising an endosomal-disrupting peptide. The peptide can include a peptide sequence of one of SEQ ID NOs: 1, 5-38, or 40-54 or 61-69. The conformationally-constrained kinked portion can be a majority portion or minority of the peptide. The peptide can include one of Formulae 1-1C, wherein: CC-Peptide includes a peptide that conformationally constrains the ED-KP; Peptide independently includes natural, unnatural, essential or non-essential aromatic, aliphatic, or other amino acids having L or D
(Continued)

configuration; ED-KP includes an endosomal-disrupting kinked peptide; Xaa, Xaa1, and Xaa2 are independently one or more natural or non-natural amino acids, essential amino acids, or non-essential amino acids, or derivatives of amino acids having L or D configuration; L1 and L2 are independently linkers; and n1, n2, n3, and n4 are independently 0-50.

20 Claims, 9 Drawing Sheets

(51) Int. Cl.
A61K 47/48 (2006.01)
A61K 47/42 (2017.01)
A61K 38/10 (2006.01)

(52) U.S. Cl.
CPC .... *A61K 47/48246* (2013.01); *C12N 2310/30* (2013.01); *C12N 2310/3513* (2013.01); *C12N 2310/3515* (2013.01)

(56) References Cited

U.S. PATENT DOCUMENTS

| 2008/0012157 | A1* | 1/2008 | Kandiyeli | B24B 37/04 257/798 |
| 2008/0039404 | A1* | 2/2008 | Hruby | C07K 7/06 514/18.3 |
| 2010/0041773 | A1 | 2/2010 | Peterson | |
| 2011/0230420 | A1* | 9/2011 | Zhao | A61K 31/00 514/19.3 |

OTHER PUBLICATIONS

Shiraishi et al. Enhanced delivery of cell-penetrating peptide-peptide nucleic acid conjugates by endosomal disruption. Nat Protoc. 2006;1(2):633-6.*

Nakase et al. Endosome-disruptive peptides for improving cytosolic delivery of bioactive macromolecules. Biopolymers. 2010;94(6):763-70.*

Jaworski et al. Detection of new sequences of peptaibol antibiotics trichotoxins A-40 by on-line liquid chromatography—electrospray ionization mass spectrometry. Journal of Chromatography A, 862 (1999) 179-189.*

Ray et al. Conformations and Mitochondrial Uncoupling Activity of Synthetic Emerimicin Fragments. Biopolymers, vol. 27, 683-701 (1988).*

Sun, et al., Selective Disruption of Early/Recycling Endosomes: Release of Disulfide-Linked Cargo Mediated by a N—Alkyl-3β-Cholesterylamine-Capped Peptide, Journal of the American Chemical Society 2008 130 (31), 10064-10065 DOI: 10.1021/ja803380a (2 pages).

Peterson, Blake R., Synthetic mimics of mammalian cell surface receptors: prosthetic molecules that augment living cells, Org. Biomol. Chem., 2005,3, 3607-3612, DOI: 10.1039/B509866A, Received Jul. 5, 2005, Accepted Aug. 11, 2005 First published online Sep. 8, 2005 (6 pages).

Hymel, et al., Synthetic cell surface receptors for delivery of therapeutics and probes, Department of Medicinal Chemistry, The University of Kansas, Lawrence, KS 66045, USA Received Dec. 23, 2011, Accepted Feb. 20, 2012, Available online Feb. 25, 2012 (14 pages).

Boonyarattanakalin et al.; Endocytic Delivery of Vancomycin Mediated by a Synthetic Cell Surface Receptor: Rescue of Bacterially Infected Mammalian Cells and Tissue Targeting in Vivo; J. Am. Chem. Soc.; 2007; vol. 129, pp. 268-269.

Gallous et al. NMR Structure of a Viral Peptide Inserted in Artificial Membranes. The Journal of Biological Chemistry. Jun. 18, 2010; vol. 285, No. 25, pp. 19409-19421.

Richardson et al. Amino Acid Preferences for Specific Locations at the Ends of α Helices. Science. Jun. 17, 1988; vol. 240, pp. 1648-1652.

Suh et al; Structural and functional implications of a proline residue in the antimicrobial peptide gaegurin; Eur. J. Biochem; 1999; vol. 266, pp. 665-674.

Flint et al. Using an Azobenzene Cross-Linker to Either Increase or Decrease Peptide Helix Content upon Trans-to-Cis Photoisomerization. Chemistry and Biology. Mar. 2002; vol. 9, pp. 391-397.

Chakrabartty et al. Helix propensities of the amino acids measured in alanine-based peptides without helix-stabilizing side-chain interactions. Protein Science. 1994; 3:843-852.

Marshall et al.; Factors governing helical preference of peptides containing multiple α,α-dialkyl amino acids; Proc. Natl. Acad. Sci. USA; Jan. 1990; vol. 87, pp. 487-491.

Lyu et al.; α-Helix stabilization by natural and unnatural amino acids with alkyl side chains; Proc. Natl. Acad. Sci. USA; Jun. 1991; vol. 88, pp. 5317-5320.

Schafmeister et al.; An All-Hydrocarbon Cross-Linking System for Enhancing the Helicity and Metabolic Stability of peptides; J. Am. Chem. Soc.; 2000; vol. 122, pp. 5891-5892.

* cited by examiner

CONFORMATIONALLY-CONSTRAINED KINKED ENDOSOMAL-DISRUPTING PEPTIDES

CROSS-REFERENCE

This patent application is a nationalization of PCT Application PCT/US2013/63250 filed Oct. 3, 2013, which PCT Application claims priority to U.S. Provisional Patent Application 61/710,289 filed Oct. 5, 2012, which provisional application and PCT Application are incorporated herein by specific reference in its entirety.

GOVERNMENT SUPPORT

This invention was made with government support under contract No. 5R01CA083831 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 2, 2013, is named K1262.10028WO01_SL.txt and is 52,250 bytes in size.

BACKGROUND

It is often difficult to deliver biologically active compounds, such as proteins, peptides, nucleic acids, drugs, and diagnostic compounds into cells across the cell membrane because cell membranes resist the passage of these compounds. One method for transmembrane delivery of exogenous molecules is based on the mechanism of receptor-mediated endocytosis (RME). RME is a major mechanism of uptake of impermeant molecules by mammalian cells (Conner, S. D.; Schmid, S. L. Nature 2003, 422, 37-44). In this process, extracellular ligands bind cell surface receptors that cluster in dynamic regions of cellular plasma membranes. By actively pinching off to form intracellular vesicles, these membrane regions are internalized, encapsulating ligand-receptor complexes in the cytoplasm. These vesicles fuse and form early (primary/sorting) endosomes that are acidified (pH about 6) by the activation of proton pumps, conditions that generally promote the dissociation of receptors from bound ligands. Free receptors often cycle back to the cell surface, generally via subsequent trafficking through related recycling endosomes (also termed the endocytic recycling compartment) (Maxfield, F. R.; McGraw, T. E. Nat. Rev. Mol. Cell. Biol. 2004, 5, 121-132).

In contrast, free ligands are typically directed to more acidic late endosomes and lysosomes (pH 5), where hydrolases and other enzymes promote their degradation. Some viruses and other intracellular pathogens exploit RME to enter cells, but these organisms avoid degradation in lysosomes by expressing pH-dependent fusogenic proteins that disrupt endosomal membranes (Lakadamyali, M.; Rust, M. J.; Zhuang, X. Microbes Infect. 2004, 6, 929-836). To escape entrapment within these membranes and gain access to the cytosol, Semliki Forest virus disrupts early endosomes whereas influenza virus disrupts late endosomes during the course of infection. Nevertheless, many exogenous molecules that are introduced into cells using RME are not able to escape degradation in the late endosomes or the lysosome.

Accordingly, it can be important in various medical therapies to destabilize an endosome in order to allow for biologically active agents to be released from the endosome and/or lysosome into cellular cytoplasm. As such, it may be advantageous to identify substances that destabilize the endosome and/or lysosome.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
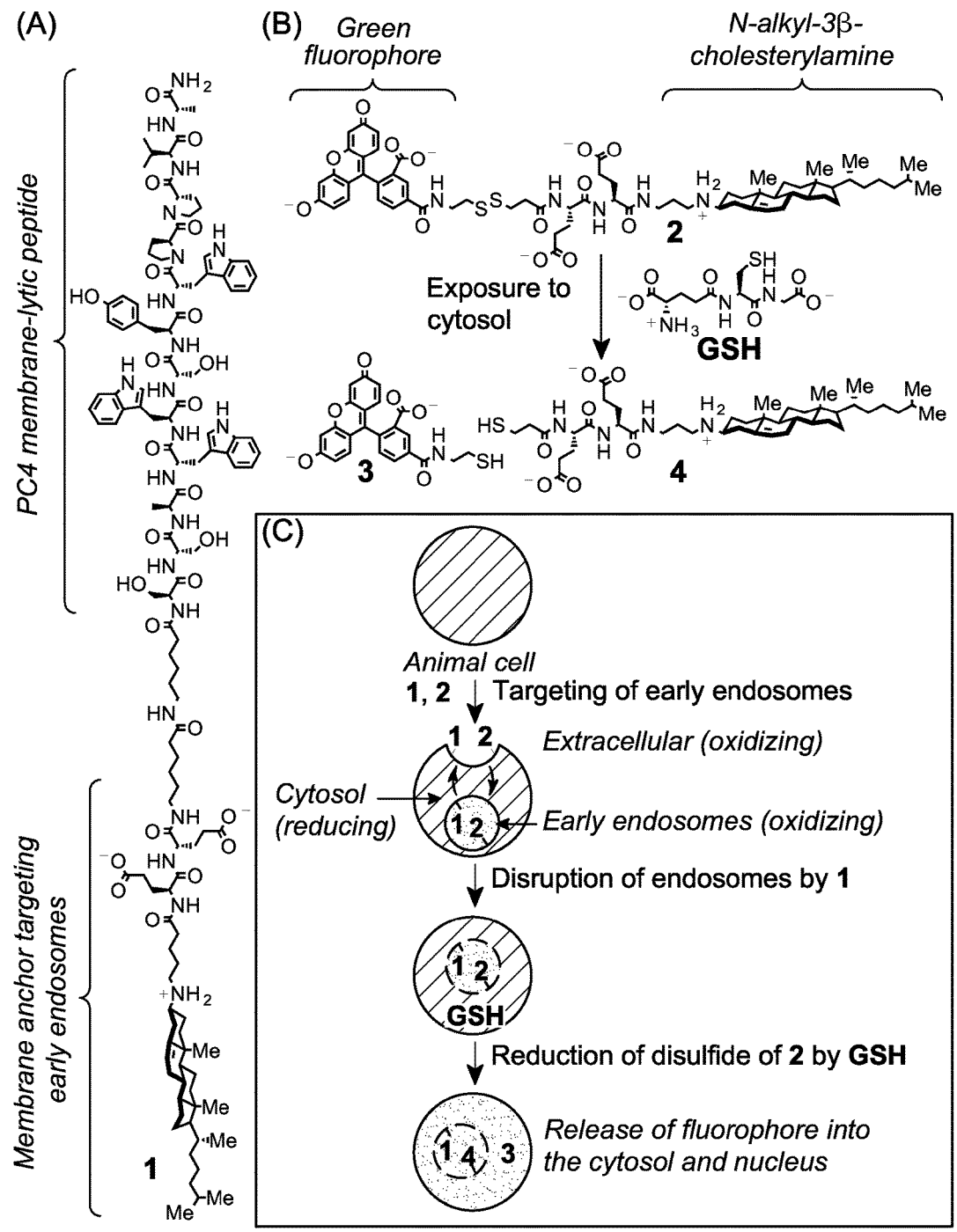
FIG. 1 shows structures of cholesterylamine-PC4 endosome disruptor (Compound 1, Panel A), a fluorescent disulfide-linked cholesterylamine (Compound 2, Panel B), and products of cleavage of Compound 2 by reduced glutathione (GSH, panel B), and Panel C shows proposed mechanism of release of the fluorescent probe Compound 3 upon disruption of early endosomes of animal cells.

Generally, the present invention relates to conformationally-constrained and kinked peptides that have endosomal disrupting properties. As such, the present invention relates to conformationally-constrained endosomal-disrupting peptides, cargo molecules thereof, cargo delivery systems thereof, and methods of manufacture and use thereof. Standard chemical synthesis techniques and peptide chemistry can be used for manufacturing the molecules of the invention. Standard agent delivery into cells and endosomal disruption techniques to release cargo into cytoplasm in in vitro or in vivo can employ the use of the molecules of the invention. Molecules of the invention can include, without limitation, conformationally-constrained endosomal-disrupting peptides and sequences thereof, conjugates thereof, cargo molecules thereof having cargo and/or targeting moieties with or without linkers with respect to the endosomal-disrupting peptide, longer polypeptides having the peptide sequence, and any other molecular constructions with the peptide sequence.

In one example, the conformationally-constrained endosomal-disrupting peptide can be coupled to a targeting moiety, such as a cell membrane-targeting moiety like a cholesterol or cholesterol derivative directly or through a linker and/or coupling group. The targeting moiety may be any protein, peptide, nucleic acid, compound or substance that facilitates RME internalization into an endosome. In another example, the conformationally-constrained endosomal-disrupting peptide can be coupled to a cargo moiety, such as a therapeutic agent, such as siRNA, small molecule drug, macromolecule drug, polypeptide, polynucleotide, or the like. In yet another example, the conformationally-constrained endosomal-disrupting peptide is linked at one end to a cargo moiety and a targeting moiety on the other end. In another example, the conformationally-constrained endosomal-disrupting peptide is linked at one end to a targeting moiety and a cargo moiety is linked to an internal region of the compound, such as near the targeting moiety, to a linker between the targeting moiety and endosomal-disrupting peptide, or to a part of the endosomal-disrupting peptide.

The conformationally-constrained endosomal-disrupting peptide can be designed based on a viral protein that facilitates endosome release. The conformationally-constrained endosomal-disrupting peptide can be configured as a membrane-lytic peptide and may include a hydrophobic, amphipathic, or other helical or non-helical sequence kinked by a proline or glycine residue. The kinked helical, non-helical, or unstructured peptide or peptidomimetic can enable the conformationally-constrained endosomal-disrupting peptide or peptidomimetic to destabilize the endosome so that cargo associated therewith can pass through pores induced in the endosome membrane. In one aspect, the conformationally-constrained endosomal-disrupting peptide is configured to mimic a viral protein that destabilizes an endosome. The conformationally-constrained endosomal-disrupting peptide can be a non-natural analogue of the dodecapeptide PC4 (sequence: SSAWWSYWPPVA; SEQ ID NO: 39). The conformationally-constrained endosomal-disrupting peptide can be linked to any targeting moiety, such as derivatives of cholesterol, other lipids, proteins, peptides, nucleic acids, carbohydrates, or other compounds which can function as cellular and endosome-targeting elements.

In one embodiment, the conformationally-constrained endosomal-disrupting peptide can include a sequence having the SSA tripeptide of PC4 replaced with helix-inducing or otherwise conformationally-constraining 2-aminoisobutyric acid (Aib) residues or derivatives thereof in order to be an active disruptor of early endosomes. In one aspect, the peptides can include covalently linking endosome disruptive peptides to both a targeting moiety (e.g., cholesteryl carbamate) and a disulfide-linked cargo (e.g., fluorophore) to provide soluble integrated delivery systems capable of release of the cargo into cellular cytosol. The conformationally-constrained endosomal-disrupting peptides disclosed here and related bioconjugates have applications as agents for cellular delivery and targeting of therapeutics and probes.

As a new strategy for delivery of cell impermeant molecules into cells, we investigated mimics of cholesterol that are designed to target membrane-active kinked peptides to early endosomes. Mimics of cholesterol were studied because free (unesterified) cholesterol is a key component of lipid bilayers of mammalian cells that resides predominantly (~60%) in the plasma membrane. Much of the remaining free cholesterol (~35%) is stored in membranes of early endosomes, particularly the endocytic recycling compartment (ERC). Constitutive cycling of cholesterol between the ERC to the plasma membrane is used to maintain homeostasis in most mammalian cells. This dynamic lipid trafficking occurs through both non-vesicular and vesicular mechanisms, and the latter process is similar to plasma membrane recycling of many cell surface receptors. We previously identified N-alkyl-3β-cholesterylamines (3β-amino-5-cholestenes) as unique synthetic mimics of cholesterol that can be avidly incorporated in the outer leaflet of plasma membranes of cells of higher eukaryotes. This incorporation occurs at least in part via a receptor-mediated process that can be inhibited by ezetimibe. Once incorporated, these compounds rapidly cycle between the plasma membrane and early/recycling endosomes, similar to many natural cell surface receptors. We found that by incorporating glutamic acid residues proximal to N-alkyl-3β-cholesterylamine and other structurally related cholesterol mimics, these compounds preferentially localize in early endosomes compared with the plasma membrane, providing a unique platform for targeting molecules to these compartments.

By linking a membrane-lytic peptide termed PC4 to N-alkyl-3β-cholesterylamine, we previously demonstrated release of a disulfide-linked fluorescent probe from early endosomes into the cytoplasm and nucleus of living mammalian cells. This novel two-component delivery system employed Compound 1 (FIG. 1, panel A) to promote cleavage of the disulfide of cholesterylamine Compound 2 and release fluorophore Compound 3 (FIG. 1, panel B) into the cytosol and nucleus of animal cells through a proposed mechanism illustrated in FIG. 1 (Panel C). Compound 4 remains after cleavage and release of Compound 3. This mechanism is based on the observation that, like the extracellular environment, some endosomes appear to be oxidizing and disruption of these compartments can allow reduced glutathione (GSH), present at high concentrations in the cytosol, to cleave disulfides targeted to the lumen of these organelles. Compared to the myriad studies of cell-penetrating peptides such as HIV-1 Tat, Penetratin, Antennapedia, and many others, that nearly universally contain multiple basic amino acid residues, the delivery approach shown in FIG. 1 is unique in that basic amino acids are not required for cellular uptake or release of cargo by these agents. Moreover, because some cell-penetrating peptides with a preponderance of basic groups exhibit substantial toxicity, the avoidance of these groups may benefit certain delivery applications.

Accordingly, the compounds of the present invention can include unnatural kinked peptides as membrane-lytic agents. The compounds of the present invention can include analogues of Compound 1 that include helix-promoting or otherwise conformationally-constrained amino acids. The design of the compounds of the invention used alanine scanning and truncation approaches to optimize release of the anionic fluorescent probe Compound 3 from early endosomes. We further constructed integrated delivery systems that combine the features of the conformationally-constrained endosomal-disrupting peptide with targeting moieties and cargo molecules for delivery into the cellular cytosol.

In one embodiment, the compounds of the invention can have improved potency, maintained or increased efficacy of disruption of early endosomes, minimized toxicity in culture, and maximized solubility. We used a combination of solution-phase and solid-phase synthesis to prepare analogues of Compound 1 including lipopeptides (Compounds 5-38) and unmodified peptides (Compounds 39-54). The structures of these compounds are shown in Tables A, B, and C. Many of these analogues include Aib residues (e.g., a stretch of contiguous Aib residues), a naturally occurring amino acid found in some antibacterial peptides. The Aib residues can be derivatives thereof, reaction products thereof, or analogues thereof having peptide linkages. The Aib residues dramatically affect peptide structure, and peptides containing Aib can adopt $3_{10}$ or alpha helical structures depending on length, the number of Aib residues, and the solvent. In peptides that equilibrate between these structures, high polarity solvents tend to favor alpha helices, whereas the $3_{10}$-helix is often observed in low polarity solvents, but Aib can also provide conformational constraint in the absence of defined helical structures.

In one aspect, Compounds 1-4 and 39 are specifically excluded from the invention.

Figure 2A:
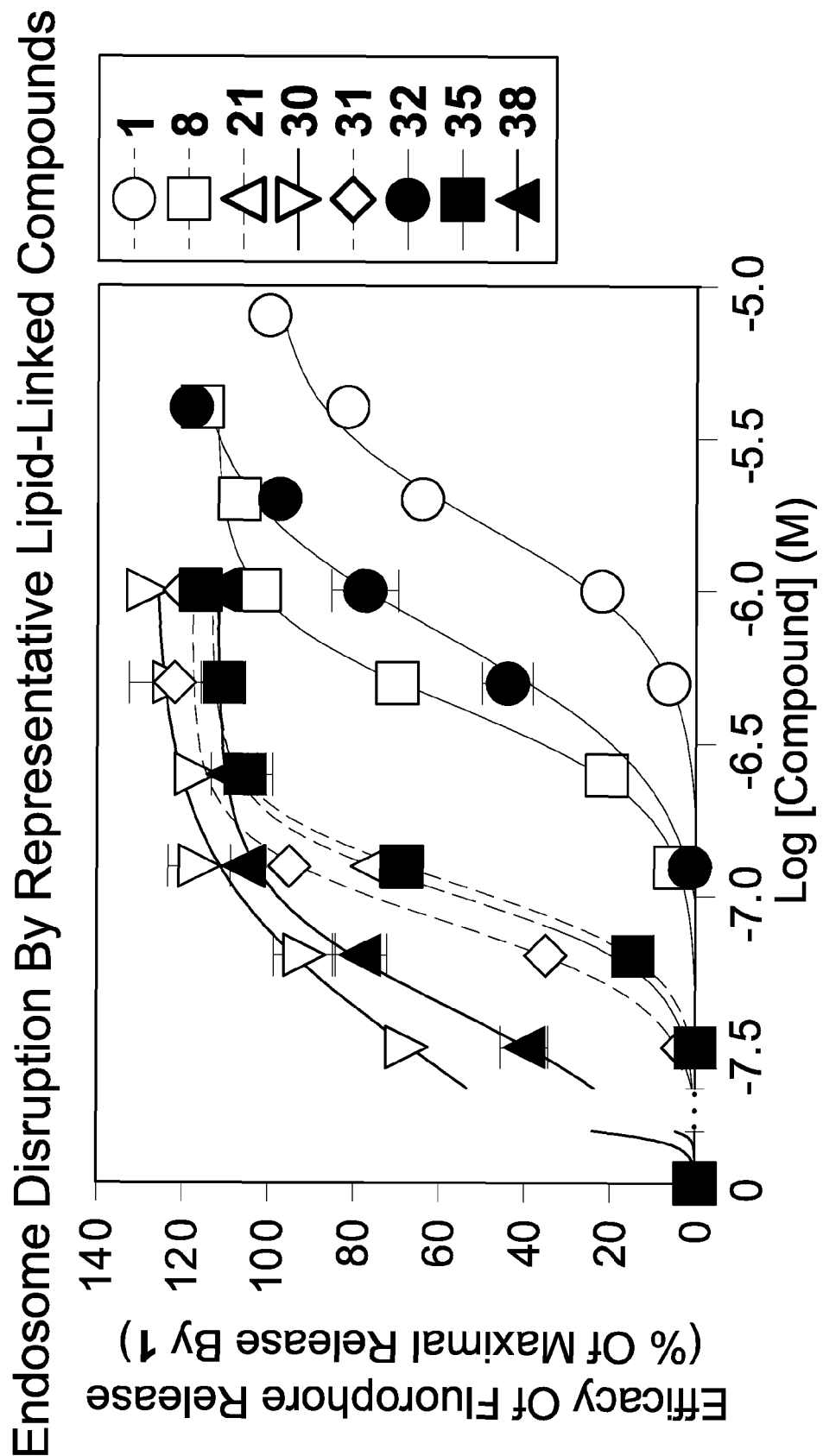
FIGS. 2A-2C include dose-response curves for disruption of endosomes of Jurkat lymphocytes by synthetic compounds of the invention.
Figure 2B:
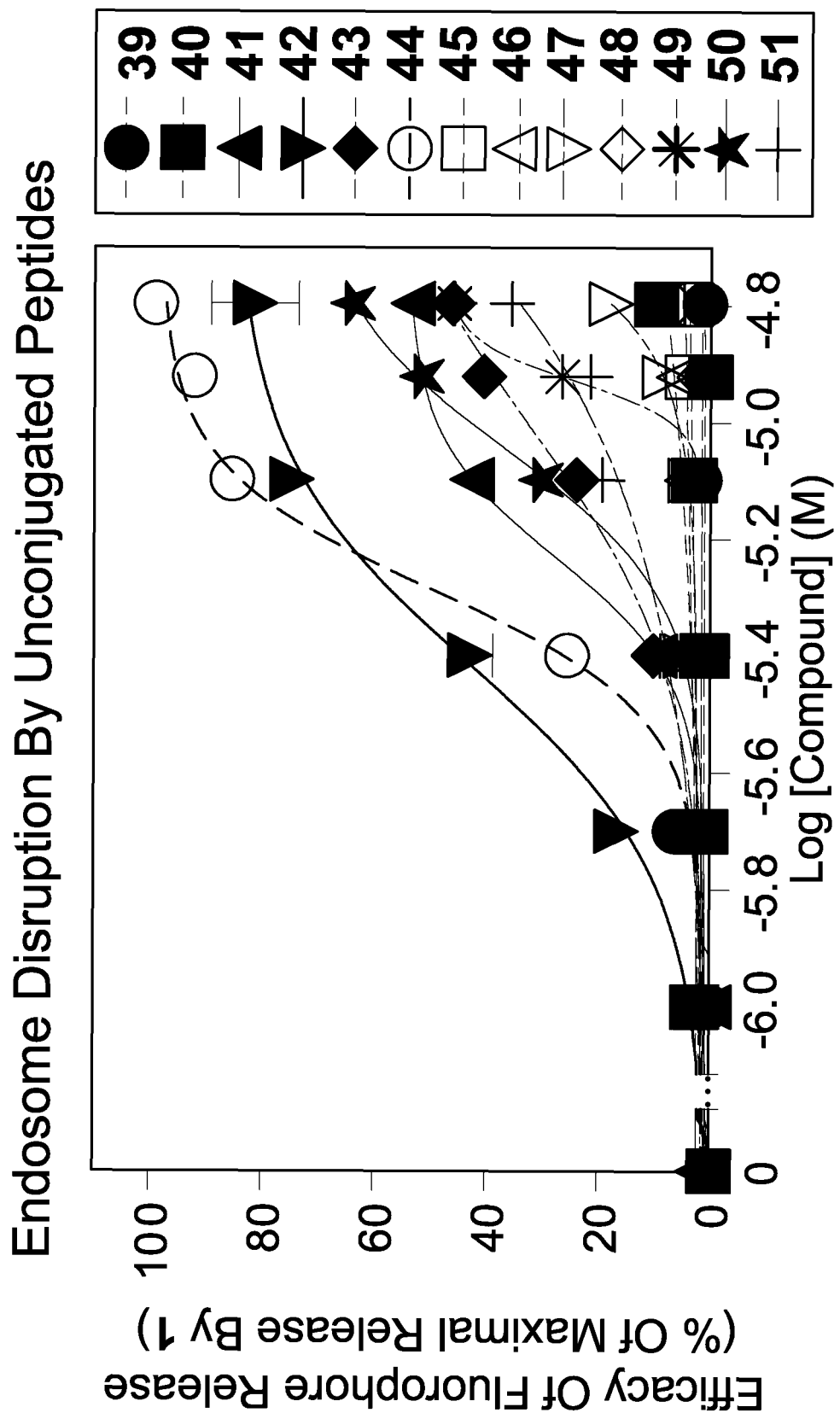
Figure 2C:
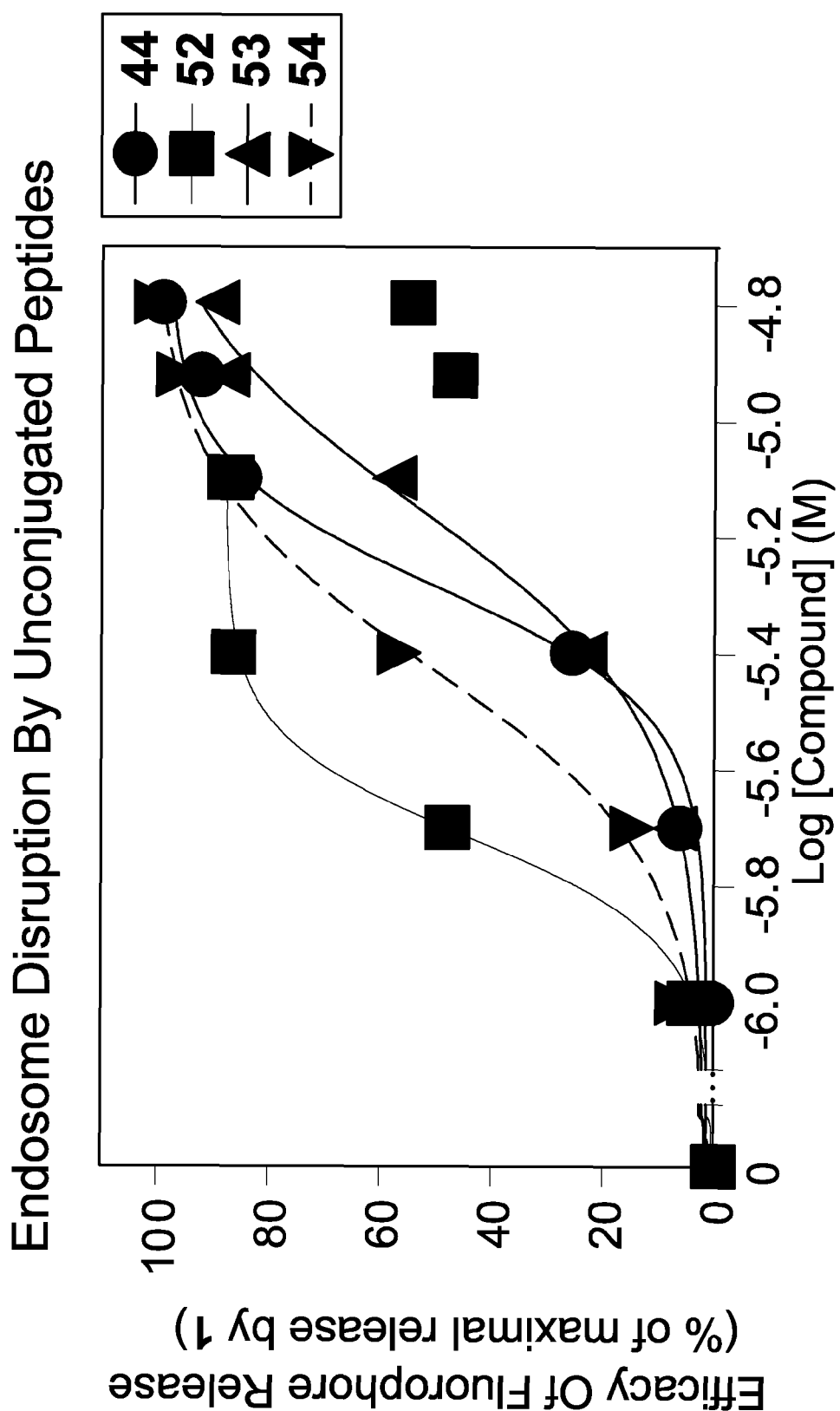

The effects of the compounds of the invention on human Jurkat leukemia cells were evaluated using flow cytometry-based assays of potency, efficacy, and toxicity. Compound potency and efficacy was typically evaluated by incubating cells with endosome disruptors and fluorescent probe Compound 2 (2.5 µM) for 14 h at 37° C. Because the fluorescence of the carboxyfluorescein of Compound 2 is quenched by the acidity of early endosomes and this fluorophore remains trapped in the cytoplasm when released from these compartments, disruption of endosomes results in enhanced cellular fluorescence that can be readily quantified. Further confirmation of release of the fluorophore was established by confocal microscopy, which revealed green fluorescence throughout the cytoplasm and nucleus for active endosome disruptive agents. Analysis of flow cytometry data by non-linear regression was used to determine $IC_{50}$ values for potency with the efficacy expressed as a percentage. The efficacy values were defined as the percentage release of carboxyfluorescein compared to the maximal release observed by Compound 1 under the same conditions. Compound 1 typically confers maximal release in this cell line at a concentration of ~8 µM. Dose-dependent effects on cellular viability after 48 h at 37° C. in culture were also measured by flow cytometry. Thermodynamic solubility was determined in phosphate buffered saline (PBS, pH 7.4) after equilibration at room temperature for 24 h. Representative dose response curves are shown in FIGS. 2A-2C, and data for representative compounds is provided in Table A and Table B and Table C.

Compounds were generated that include a targeting moiety, such as a cholesterol derivative, where the generic structures of the formulae of the compounds is provided below in Structures A, A1, A2, X, B, O, U, and Z (notice Structure O is not oxygen). Structure A is a cholesterol derivative with a linker of 5-aminopentanamide or 5-aminopentanoic acid or reaction product thereof or derivative thereof between the chol and peptide R. Structure A1 is a palmitic acid derivative with a linker of 5-aminopentanamide or 5-aminopentanoic acid or reaction product thereof or derivative thereof between the chol and peptide R'. Structure A2 is a cholesteryl carbamate derivative with linker of 3-aminopropanamide or 3-aminopropanic acid or reaction product thereof or derivative thereof between the chol and peptide R'. Structure X is a 6-aminohexanamide or 6-aminohexanoic acid or ε-Ahx amino acid or reaction product thereof or derivative thereof, which can be considered a nonstandard amino acid. B is 3-aminopropanamide or 3-aminopropanoic acid or reaction product thereof or derivative thereof, which can be considered a nonstandard amino acid. O is 3-(2-(2-(2-aminoethoxy)ethoxy)ethoxy)propanamide or 3-(2-(2-(2-aminoethoxy)ethoxy)ethoxy)propanoic acid or mini-PEG amino acid or reaction product thereof or derivative thereof, which can be considered a nonstandard amino acid. U is 2-amino-2-methylpropanamide or 2-amino-2-methylpropanoic acid or 2-aminoisobutyric acid or Aib amino acid or reaction product thereof or derivative thereof, which can be considered a nonstandard amino acid. Z is (S)-2-aminopent-4-ynamide or (S)-2-aminopent-4-ynoic acid or vinylglycine or reaction product thereof or derivative thereof, which can be considered a nonstandard amino acid. Structures X, B, O, U, and Z can serve as linkers in the peptide, and may be considered nonstandard amino acids for peptide descriptions and sequence listing purposes, and may include or form amide bonds common with amino acids in peptides. The structures of Structures A, A1, A2, X, B, O, U, and Z are illustrated below. The R, R', and R" of Structures A, A1, and A2 are provided in Table A.

Also, R, R', and R" can include another linker and the peptide so that the linker further separates the targeting moiety from the peptide. As such, the linker shown in Structures A, A1, and A2 can include an extended linker. Alternatively, the illustrated linker coupled to the R, R', and R" can be substituted or exchanged for a different linker. Such a linker between the targeting moiety and peptide can be any type of linker, including biodegradable and biostable linkers, and linkers which can include the cargo coupled thereto.

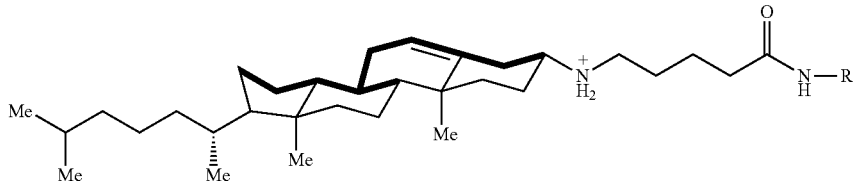

Structure A

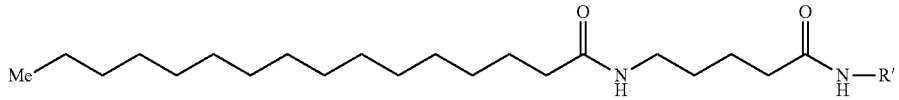

Structure A1

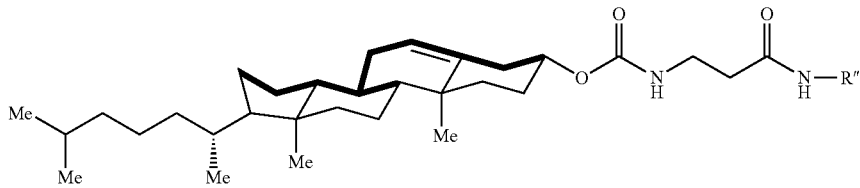

Structure A2

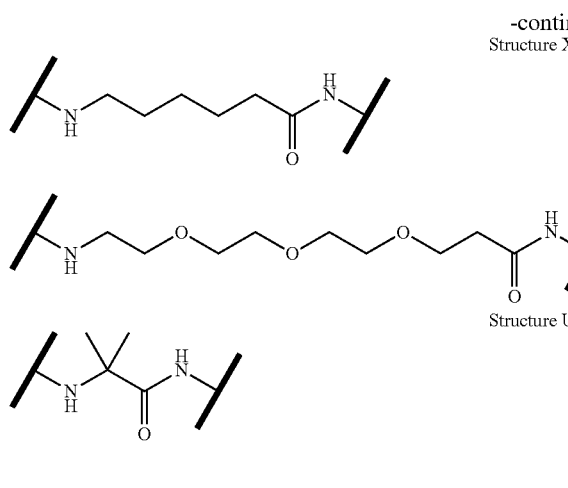

The compounds of Structures A, A1, and A2 can include peptide sequences that are lipid-linked endosome disruptors. They can include a lipidic-targeting moiety (T), a linker (L), and conformationally-constrained endosomal-disrupting peptide (CCEDP) to form T-L-EDP. The linker L can include a cargo molecule coupled thereto, as shown herein, where the cargo can be any cargo for delivery into the cytoplasm.

In Tables A, B, and C, the natural amino acids are represented by single letter codes, with codes for nonstandard amino acids, and X, B, O, U, and Z are defined above. Amino acid residues shown in bold represent changes from sequences directly above in the Table A. Residues underlined in italics flank (see Compound 10) deleted amino acids compared to sequences directly above in Table A.

It should be recognized that the peptide sequences of Compounds 1 and 5-69 of Table A and Table B and Table C and the structures may be used alone. That is, the R, R', and R" do not have to be linked to a targeting moiety. Accordingly, the peptide sequences of Compounds 5-69 can include an amine end, such as $NH_2$ or $NH_3^+$ instead of the targeting moiety. Also, the targeting moiety of Compounds 5-38 and 55-60 can be included with a different end group or cap, such as an acetyl group (e.g., Ac). Also, the targeting moiety of Compounds 5-38 and 55-60 can be exchanged with a cargo substance. Correspondingly, the $NH_3^+$ or Ac of Compounds 39-54 and 61-68 can be exchanged for a targeting moiety or cargo substance.

The peptide sequences of Compounds 5-38 and 40-69 are novel conformationally-constrained peptides. As such, the peptide sequences of Compounds 1 and 5-69 are Peptides 1 and 5-69. The Peptides 1 and 5-69 are identified by the amino acid sequences of Sequences 1 and 5-54 and 61-69. As such, the Compounds 1 and 5-69, Peptides 1 and 5-69, and Sequences 1 and 5-54 and 61-69 correlate, and include SEQ ID NOs: 1 and 5-54 and 61-69 of the Sequence Listing.

In one embodiment, the $CONH_2$ of Compounds 1 and 5-69 and Peptides 1 and 5-54 and 61-69 can be coupled to a targeting moiety. The targeting moiety can be any as described herein, such as a cholesterol derivative or other. However, either end of the peptides of Compounds and Peptides 1 and 5-54 and 61-69 may be coupled to a targeting moiety and the other coupled to a cargo substance.

In one embodiment, the $CONH_2$ of Compounds 1 and 5-69 and Peptides 1 and 61-69 can be coupled to a cargo substance. The cargo substance can be any agent to be delivered into a cell. Such cargo substances can be drugs, such as small molecule drugs, nucleic acid drugs (e.g., siRNA), macromolecule drugs or protein drugs, or combinations thereof as well as any other cargo including toxins. The cargo can also be a reporter, such as a fluorophore or enzyme substrate.

In one embodiment, an internal amino acid or other linker moiety of Compounds 1 and 5-69 and Peptides 1 and 5-54 and 61-69 can be coupled to a cargo substance, such as shown in Compounds 55-60. The cargo substance can be any agent to be delivered into a cell. Such cargo substances can be drugs, such as small molecule drugs, nucleic acid drugs (e.g., siRNA), macromolecule drugs or protein drugs, or combinations thereof as well as any other cargo including toxins. The cargo can also be a reporter, such as a fluorophore or enzyme substrate. While a fluorophore is shown in Compounds 55-60, any cargo, such as a drug, may also be coupled in the same manner.

In one embodiment, either the C-terminus or N-terminus of the peptides can have additional peptides or polypeptides. That is, the peptide sequences shown can be internal to a polypeptide.

Figure 4A:
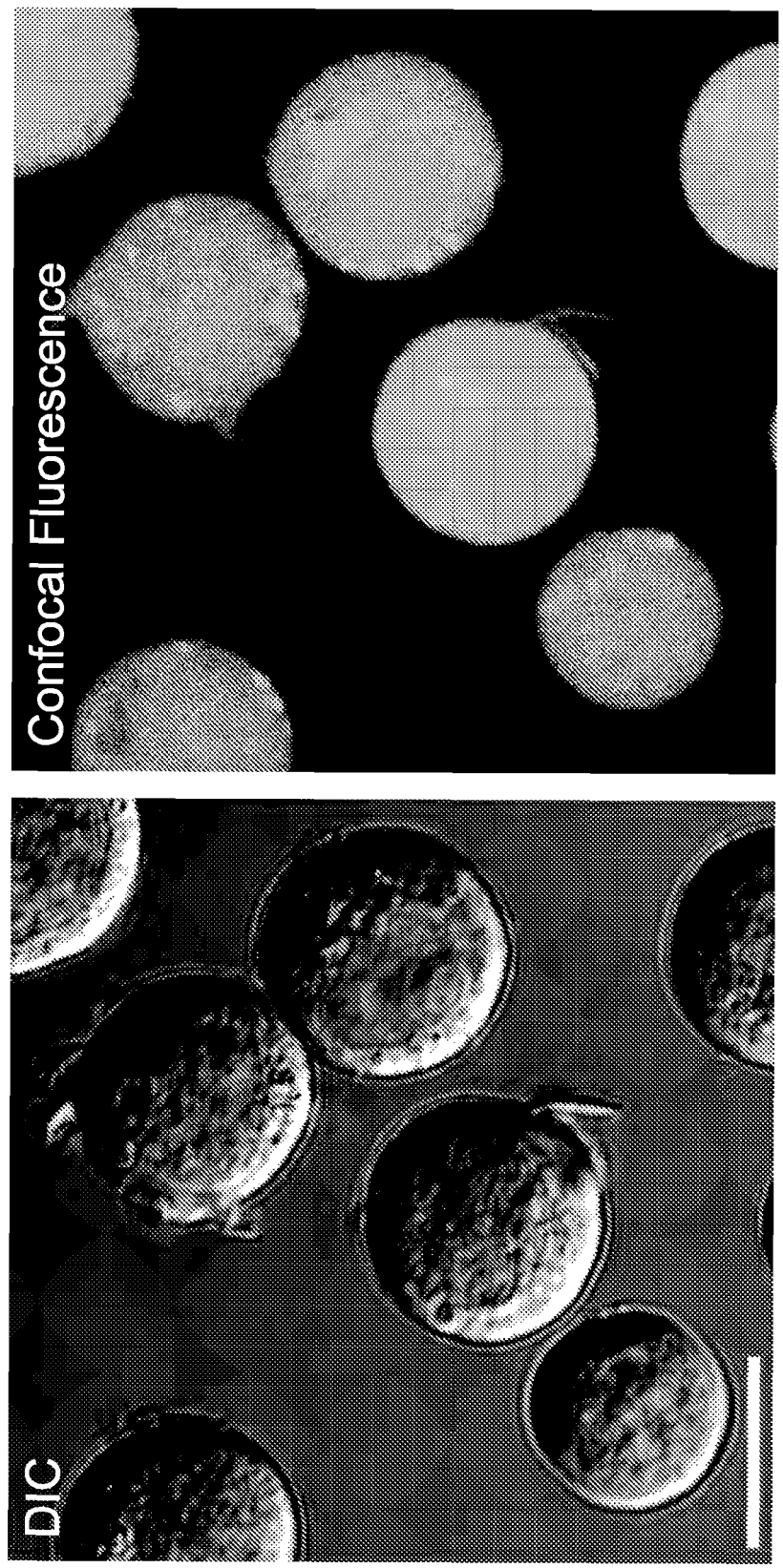
FIG. 4A includes micrographs obtained after treatment with Compound 59.
Figure 4B:
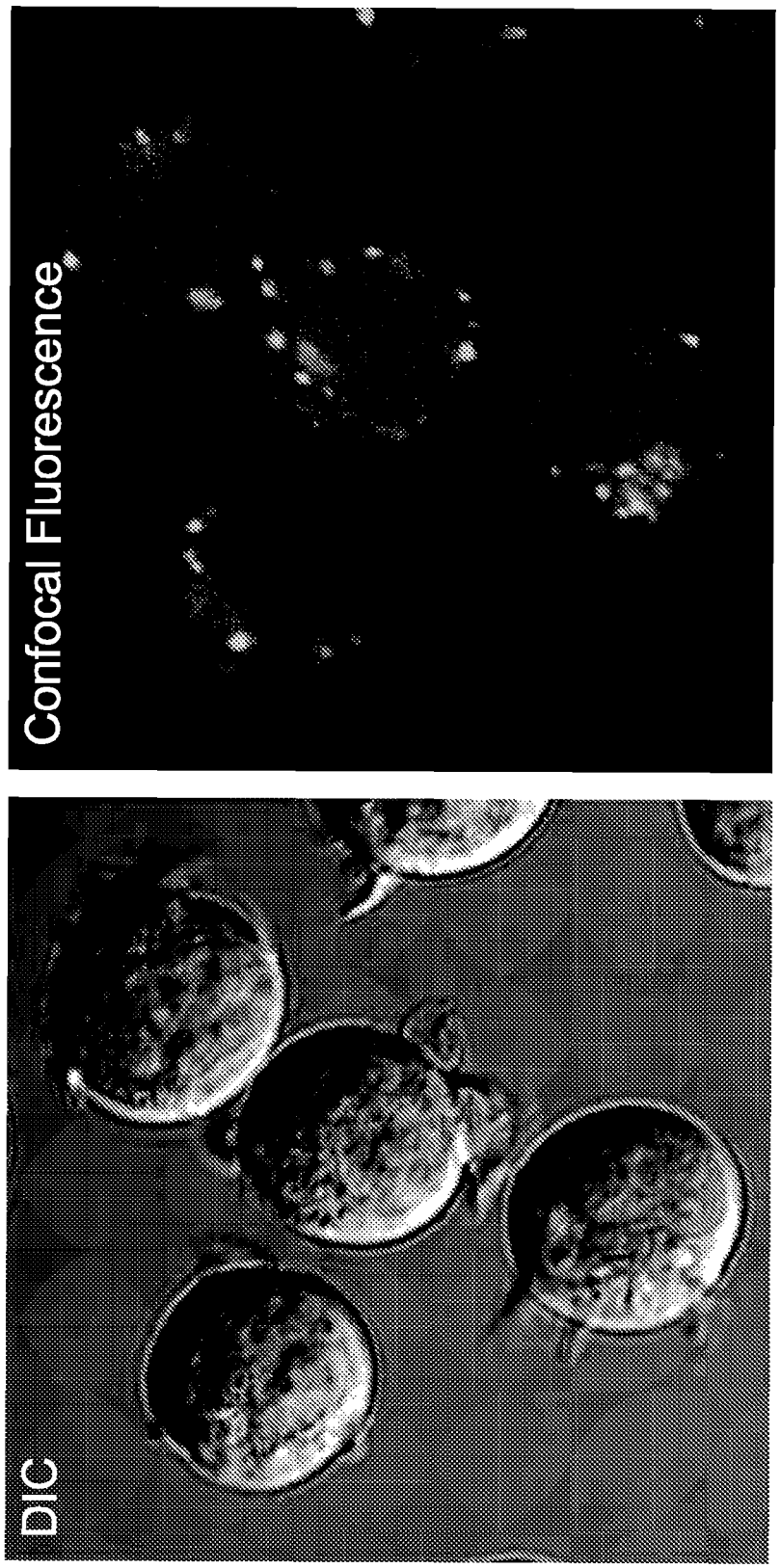
FIG. 4B includes micrographs obtained after treatment with Compound 60.

FIGS. 4A-4B show dose-response curves for disruption of endosomes of Jurkat lymphocytes by synthetic compounds. Cells were treated with fluorescent molecular probe Compound 2 (2.5 µM) and endosome disruptors for 14 hours at 37° C. Enhanced cellular fluorescence resulting from release of the pH-sensitive fluorophore Compound 3 into the cytoplasm was quantified by flow cytometry.

Figure 3:
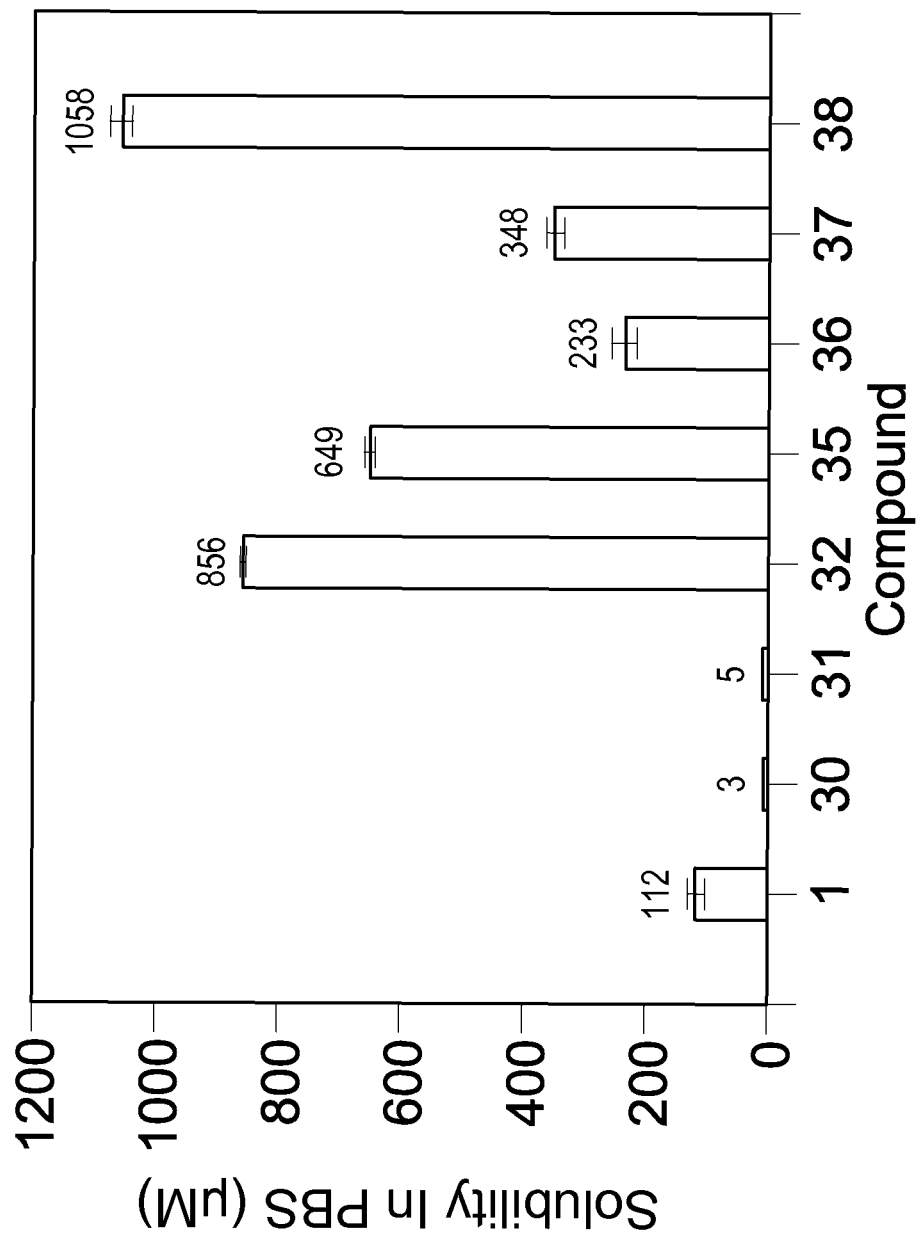
FIG. 3 includes a graph that shows solubility of compounds of the invention in PBS.

FIG. 3 shows the thermodynamic solubility values for representative compounds in PBS (pH 7.4) after equilibration for 24 hours.

Table 1 shows the potency, efficacy, toxicity, and solubility of representative synthetic endosome disruptors. The # represents the compound number in accordance with Tables A, B, and C. Concentrations of compound stock solutions were determined by absorbance measurements at 280 nm. Efficacy was determined as % change in cellular fluorescence relative to the maximal response of Compound 1, defined as 100%. Potencies and efficacies in Jurkat lymphocytes were measured by flow cytometry after treatment of cells with the compounds listed and the fluorescent probe Compound 2 (2.5 µM) for 14 hours. Toxicity to this cell line was determined by flow cytometry analysis of light scattering and counterstaining with PI after treatment for 48 h at 37° C. in culture. Thermodynamic solubility in PBS (pH 7.4, ±S.D.) was measured by sonication of 1 mL solutions containing visible solid for 30 minutes at room temperature (22° C.), gentle rocking of these samples for 24 hours at room temperature (22° C.), centrifugation for 1 hour at 16000 g, and absorbance measurements of the supernatant at 280 nm to determine concentration based on calculated extinction coefficients. Values in parentheses represent 95% confidence intervals. N.D., not determined.

TABLE A

| Compound NO. SEQ ID NO. | | |
|---|---|---|
| 1, | R = | EEXXSSAWWSYWPPVA-CONH$_2$ |
| 5, | R = | EEXXAAAWWAYWPPVA-CONH$_2$ |
| 6, | R = | BEEXSSAWWSYWPPVA-CONH$_2$ |
| 7, | R = | BEEXAAAWWAYWPPVA-CONH$_2$ |
| 8, | R = | BEEXXAAAWWAYWPPVA-CONH$_2$ |
| 9, | R = | BEEXUUUWWAYWPPVA-CONH$_2$ |
| 10, | R = | BEEXU*UW*WAYWPPVA-CONH$_2$ |
| 11, | R = | BEEXUUUWWAYWPPV-CONH$_2$ |
| 12, | R = | BEEXUUUAWAYWPPVA-CONH$_2$ |
| 13, | R = | BEEXUUUWAAYWPPVA-CONH$_2$ |
| 14, | R = | BEEXUUUWWAAWPPVA-CONH$_2$ |
| 15, | R = | BEEXUUUWWAYAPPVA-CONH$_2$ |
| 16, | R = | BEEXUUUWWAYWAPVA-CONH$_2$ |
| 17, | R = | BEEXUUUWWAYWPAVA-CONH$_2$ |
| 18, | R = | BEEXUUUWWAYWPPAA-CONH$_2$ |
| 19, | R = | BEEXUUUWWAWWPPVA-CONH$_2$ |
| 20, | R = | BEEXUUUUWWAYWPPVA-CONH$_2$ |
| 21, | R = | BEEXXUUUWWAYWPPVA-CONH$_2$ |
| 22, | R = | BEEXXUUUUFFAFFPPVA-CONH$_2$ |
| 23, | R = | BEEXXUUUUYYAYYPPVA-CONH$_2$ |
| 24, | R = | BEEXXUUUUYYYYYPPVA-CONH$_2$ |
| 25, | R = | BEEXXUUUUYYAYYPPVV-CONH$_2$ |
| 26, | R = | BEEOOUUUUWWAYWPPVA-CONH$_2$ |
| 27, | R = | BEEOOUUUUWWAYWPPVAA-CONH$_2$ |
| 28, | R = | BEEOOUUUUYYAYYPPVV-CONH$_2$ |
| 29, | R = | BEEOOUUUUYYYYYPPW-CONH$_2$ |
| 30, | R = | BEEZOOUUUUYYAYYPPW-CONH$_2$ |
| 31, | R = | BEEZOOUUUUWWAYWPPVA-CONH$_2$ |
| 32, | R' = | BEEOOUUUUWWAYWPPVA-CONH$_2$ |
| 33, | R" = | BZOOUUUUWWAYWPPVA-CONH$_2$ |
| 34, | R" = | BEEOOUUUUWWAYWPPVA-CONH$_2$ |
| 35, | R" = | BEEZOOUUUUWWAYWPPVA-CONH$_2$ |

TABLE A-continued

| Compound NO. SEQ ID NO. | | |
|---|---|---|
| 36, | R" = | BEEZOOUUUUWWAYWPPVV-CONH$_2$ |
| 37, | R" = | BEEZOOUUUUWWAYYPPVV-CONH$_2$ |
| 38, | R" = | BEEZOOUUUUYYAYYPPVV-CONH$_2$ |

TABLE B

| Compound NO. SEQ ID NO. | |
|---|---|
| 39, | Ac-SSAWWSYWPPVA-CONH$_2$ |
| 40, | Ac-AAAWWAYWPPVA-CONH$_2$ |
| 41, | Ac-UUUWWAYWPPVA-CONH$_2$ |
| 42, | Ac-UUUUWWAYWPPVA-CONH$_2$ |
| 43, | H3N+-UUUUWWAYWPPVA-CONH$_2$ |
| 44, | H$_3$N$^+$-UUUUWWAYWPPVV-CONH$_2$ |
| 45, | H$_3$N$^+$-UUUUAWAYWPPVV-CONH$_2$ |
| 46, | H$_3$N$^+$-UUUUWAAYWPPVV-CONH$_2$ |
| 47, | H$_3$N$^+$-UUUUWAAWPPVV-CONH$_2$ |
| 48, | H$_3$N$^+$-UUUUWWAYAPPVV-CONH$_2$ |
| 49, | H$_3$N$^+$-UUUUWWAYWAPVV-CONH$_2$ |
| 50, | H$_3$N$^+$-UUUUWWAYWPAVV-CONH$_2$ |
| 51, | H$_3$N$^+$-UUUUWWAYWPPAV-CONH$_2$ |
| 52, | H$_3$N$^+$-UUUUYWAWWPPVV-CONH$_2$ |
| 53, | H$_3$N$^+$-UUUUWYAWWPPVV-CONH$_2$ |
| 54, | H$_3$N$^+$-UUUUWWAWYPPVV-CONH$_2$ |

TABLE C

| Compound NO. SEQ ID NO. | |
|---|---|
| 61, | Ac-UUUUUWWAYWPPVA-CONH$_2$ |
| 62, | Ac-UUUUYYAYYPPVV-CONH$_2$ |
| 63, | Ac-UUUUWWAYWPPVV-CONH$_2$ |
| 64, | Ac-UUUUHHAHHPPVV-CONH$_2$ |
| 65, | Ac-UUUUWWAYWPPVL-CONH$_2$ |
| 66, | Ac-UUUUWWAYWPPLV-CONH$_2$ |
| 67, | Ac-UUUUWWAYWPPLL-CONH$_2$ |
| 68, | Ac-UUUUWWGYWPPVA-CONH$_2$ |
| 69, | Ac-UUUUYYAYYPPVV-CONH$_2$ |

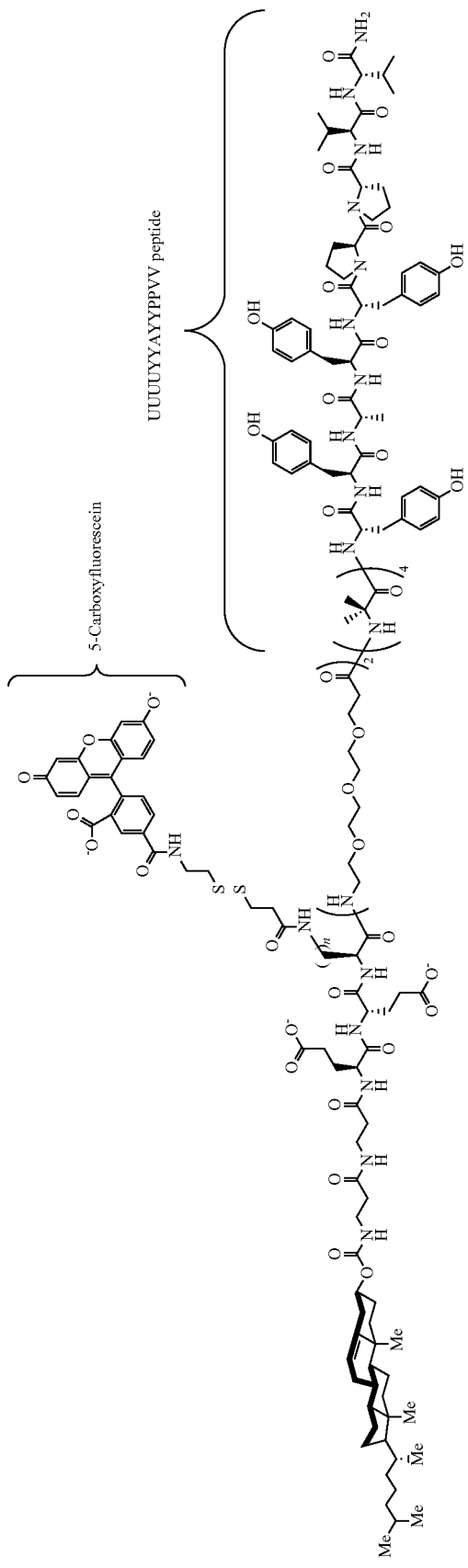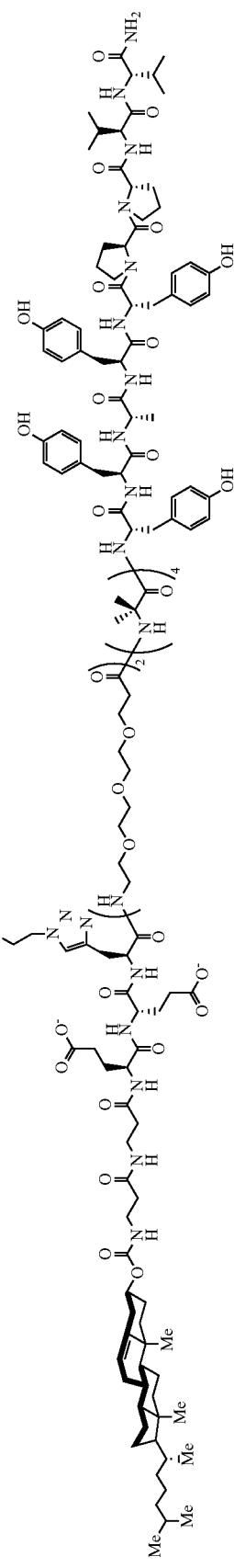

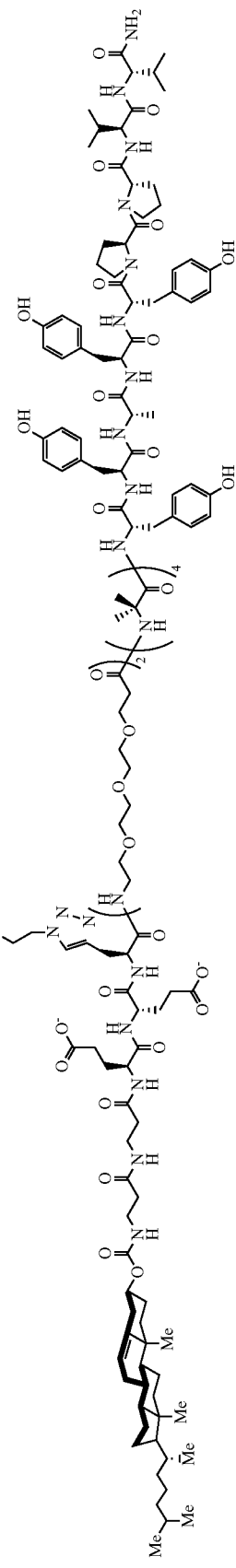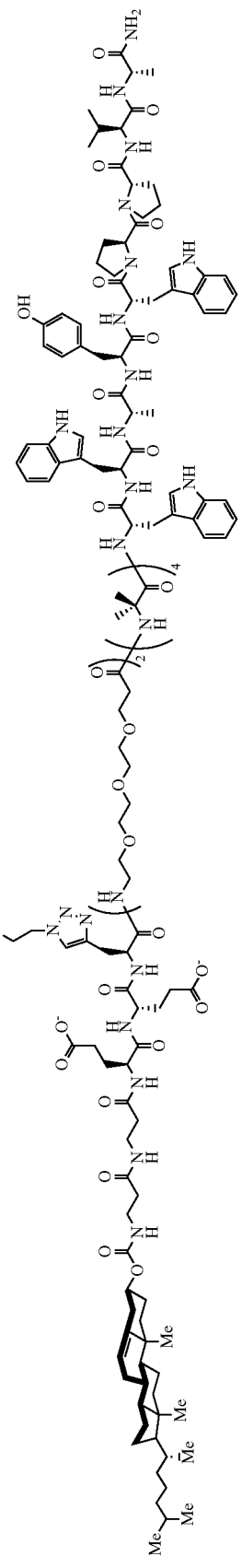

-continued
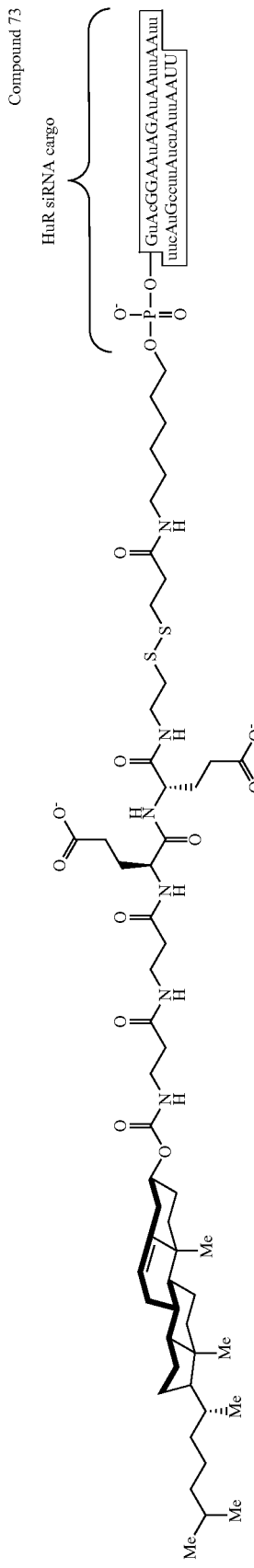
(Compound 73 discloses the siRNA sequences as SEQ ID NOS 77 and 76, respectively, in order of appearance)
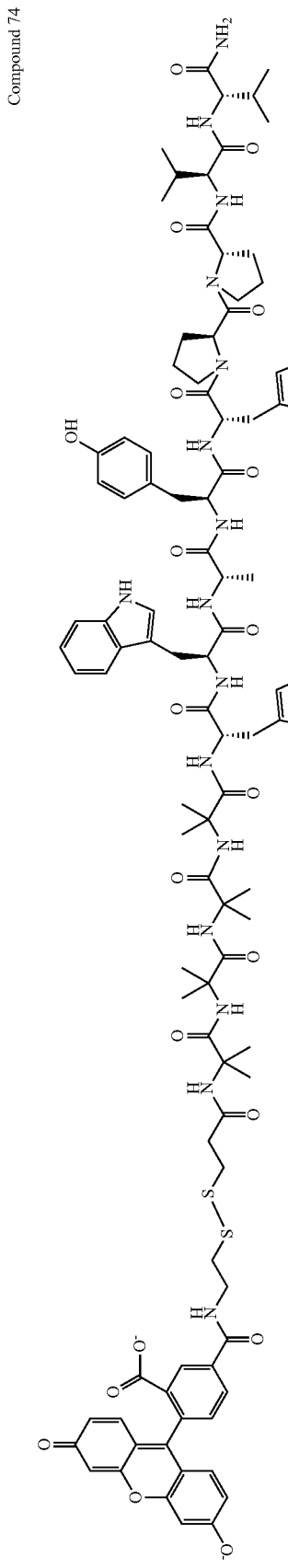
(Compound 74 discloses "UUUUYYAYYPPVV" as SEQ ID NO: 69)

Compounds 55-60 and 70-72 and 73 include the peptide sequence of Compound 69-UUUUYYAYYPPVV-CONH$_2$ (SEQ ID NO: 69). Compounds 72 and 73 include the HuRsiRNA having SEQ ID NOS: 75-77. It should be noted that the targeting moiety and cargo can be exchanged for any targeting moiety and cargo. The peptide can be exchanged with other peptides in accordance with the invention.

Some of the analogues investigated (Compounds 5-31) included the N-alkyl-3β-cholesterylamine membrane anchor present in the endosome disruptor (Compound 1). Replacement of the SSA tripeptide of Compound 1 with a more hydrophobic and helix-promoting AAA tripeptide enhanced potency by fourfold (compare Compound 1 with Compound 5). Inclusion of a beta-alanine near the N-terminus further enhanced efficacy (compare Compound 8 with Compound 5). Substitution of the N-terminal AAA tripeptide of Compound 7 with the conformationally-constrained UUU (U=Aib) sequence enhanced potency with some loss of efficacy that may be due to shortening of the constrained peptide (compare Compound 7 with Compound 9). Comparison of Compound 9 with Compound 10 and Compound 11 indicated that truncation of a single residue at the N-terminus or C-terminus of the core PC4-related sequence reduced potency and/or efficacy.

Analysis of the alanine-scanning analogues Compounds 12-18 compared to the reference Compound 9 revealed that many of the aromatic amino acids are helpful for high activity/potency. Additionally, the kinking PP dipeptide (e.g., di-proline sequence) provides maximal activity, but agents with a single proline residue (e.g., Compound 16 and Compound 17) retain substantial activity. These studies also revealed that the hydrophobic valine near the C-terminus is particularly helpful. Further extension of the UUU sequence by one Aib to obtain UUUU (SEQ ID NO: 2) enhanced potency by tenfold (compare Compound 19 with Compound 20).

TABLE 1

| # | Potency (EC$_{50}$, μM) | Efficacy (% of max. 1) | Toxicity (IC$_{50}$, μM) | Solubility (aq., μM) |
| --- | --- | --- | --- | --- |
| 1 | 1.6 (1.4-1.9) | 100 (88-113) | 9 (8-9) | 112 ± 13 |
| 5 | 0.4 (0.4-0.5) | 100 (95-105) | 14 (13-16) | 10 ± 1 |
| 6 | 3.5 (3.3-3.6) | 94 (89-98) | N.D. | N.D. |
| 7 | 1.0 (0.9-1.1) | 99 (90-107) | 16 (15-16) | N.D. |
| 8 | 0.4 (0.4-0.5) | 113 (103-122) | 9 (8-9) | N.D. |
| 9 | 0.4 (0.3-0.5) | 87 (80-92) | 11 (10-12) | 12 ± 1 |
| 10 | 0.9 (0.8-1.0) | 97 (86-107) | 15 (15-15) | N.D. |
| 11 | 0.8 (0.8-0.9) | 71 (66-77) | 15 (15-16) | N.D. |
| 12 | 0.4 (0.3-0.5) | 99 (90-108) | 14 (13-14) | N.D. |
| 13 | 0.7 (0.6-0.8) | 97 (89-104) | 16 (15-16) | N.D. |
| 14 | 1.2 (0.8-1.9) | 51 (39-63) | N.D. | N.D. |
| 15 | N.D. | <50 | N.D. | N.D. |
| 16 | 1.6 (1.3-2.0) | 55 (47-63) | N.D. | N.D. |
| 17 | 2.1 (1.8-2.5) | 55 (47-64) | N.D. | N.D. |
| 18 | N.D. | <50 | N.D. | N.D. |
| 19 | 1.0 (0.9-1.2) | 88 (79-97) | 20 (18-21) | N.D. |
| 20 | 0.1 (0.09-0.13) | 109 (99-118) | 15 (15-15) | N.D. |
| 21 | 0.1 (0.08-0.12) | 112 (102-122) | 9 (8-9) | N.D. |
| 22 | >10 | <50 | N.D. | N.D. |
| 23 | 0.10 (0.09-0.11) | 74 (701-78) | 4 (4-4) | N.D. |
| 24 | 0.09 (0.07.0.10) | 74 (65-83) | 5 (4-5) | N.D. |
| 25 | 0.09 (0.09-0.10) | 109 (104-114) | 9 (9-9) | 22 ± 2 |
| 26 | 0.1 (0.06-0.15) | 123 (113-134) | 8 (8-9) | 14 ± 2 |
| 27 | 0.2 (0.1-0.2) | 81 (74-87) | 3 (3-3) | N.D. |
| 28 | 0.06 (0.05-0.07) | 122 (111-133) | 3 (3-4) | 63 ± 28 |
| 29 | 0.08 (0.07-0.09) | 125 (115-135) | 3 (3-3) | 90 ± 2 |
| 30 | 0.03 (0.02-0.04) | 127 (110-144) | 2 (2-2) | 3 ± 1 |
| 31 | 0.08 (0.7-0.9) | 119 (109-130) | 4 (3-4) | 5 ± 1 |
| 32 | 0.7 (0.5-1.0) | 121 (95-149) | 16 (15-17) | 856 ± 2 |
| 33 | 0.13 (0.12-0.15) | 129 (117-141) | >100 | 2 ± 1 |
| 34 | 0.10 (0.09-0.12) | 102 (92-111) | 17 (17-17) | 405 ± 20 |

TABLE 1-continued

| # | Potency (EC$_{50}$, μM) | Efficacy (% of max. 1) | Toxicity (IC$_{50}$, μM) | Solubility (aq., μM) |
| --- | --- | --- | --- | --- |
| 35 | 0.11 (0.10-0.12) | 114 (110-119) | 13 (13-13) | 649 ± 11 |
| 36 | 0.06 (0.06-0.07) | 128 (122-133) | 13 (13-14) | 233 ± 21 |
| 37 | 0.04 (0.04-0.05) | 130 (124-135) | 3 (3-4) | 348 ± 13 |
| 38 | 0.04 (0.04-0.05) | 112 (102-122) | 8 (8-8) | 1058 ± 19 |
| 39 | N.D. | <<50 | N.D. | 173 ± 11 |
| 40 | N.D. | <<50 | N.D. | N.D. |
| 41 | 5.9 (5.5-6.3) | 53 (50-56) | >100 | 24 ± 3 |
| 42 | 5.3 (4.9-5.9) | 85 (78-92) | >100 | 11 ± 1 |
| 43 | 10 (6-15) | 64 (38-90) | N.D. | N.D. |
| 44 | 5.2 (4.8-5.5) | 97 (94-102) | N.D. | 22 ± 1 |
| 45 | N.D. | <<50 | N.D. | N.D. |
| 46 | N.D. | <<50 | N.D. | N.D. |
| 47 | N.D. | <<50 | N.D. | N.D. |
| 48 | N.D. | <<50 | N.D. | N.D. |
| 49 | 12 (12-12) | 45 (42-52) | N.D. | N.D. |
| 50 | 9 (8-10) | 71 (62-81) | N.D. | N.D. |
| 51 | N.D. | <50 | N.D. | N.D. |
| 52 | 1.9 (1.8-2.1) | 87 (83-93) | N.D. | N.D. |
| 53 | 7.1 (5.6-9.1) | 104 (79-128) | N.D. | N.D. |
| 54 | 3.8 (3.5-4.1) | 100 (94-107) | N.D. | N.D. |

Replacement of all of the more polar Trp and Tyr amino acids with Phe was not tolerated (compare Compound 21 with Compound 22), but potency was retained with some reduction in efficacy when the Trp residues were replaced by Tyr (compare Compound 21 with Compound 23). This loss of efficacy was overcome by installation of Val at the C-terminus (compare Compound 23 with Compound 25).

In an attempt to improve solubility, the ε-Ahx-ε-Ahx motif (e.g., XX dipeptide) of Compound 21 was replaced by a dipeptide derived from two mini-PEG amino acids (e.g., OO dipeptide). This change enhanced efficacy (compare Compound 21 with Compound 26), but the solubility of Compound 26 in PBS continued to be much lower (e.g., 14 μM) than the parent Compound 1 (e.g., 112 μM). Higher potency and solubility were achieved by further substituting the more hydrophobic Trp residues with the more polar Tyr (compare Compound 26 with Compound 28 and Compound 29), but none of these compounds were more soluble than Compound 1. The data provides enhanced potency of tyrosine-containing YYAYY peptides (SEQ ID NO: 3) over analogous tryptophan-containing WWAYW peptides (SEQ ID NO: 4), demonstrating greater affinity of tyrosine for insertion into biological membranes compared with tryptophan.

Compounds 30 and 31 included propargylglycine as an alkyne for potential coupling to cargo using Cu-catalyzed Huisgen 1,3-dipolar cycloaddition reactions with azides. These compounds represented two of the most potent and effective endosome disruptors, but showed low solubility in PBS (<5 μM). However, solubility can be enhanced by a modified linker that includes hydrophilic moieties, such as a PEG linker or a linker that includes PEG.

To evaluate the properties of endosome disruptors linked to other lipids, the palmitic acid derivative Compound 32 and cholesteryl carbamates Compounds 33-38 were synthesized. These compounds proved to be much more soluble in PBS than the corresponding cholesterylamines (See FIGS. 2A-2C and Table 1). The palmitic acid derivative Compound 32 was sevenfold less potent than a structurally similar cholesterylamine Compound 26, but remarkably was sixty-fold more soluble in PBS (856 μM). Fortuitously, the analogous cholesteryl carbamate Compound 34 retained high potency/efficacy, comparable to Compound 26, while maintaining high solubility in PBS (405 μM). Studies of the solubility of simpler model systems that replaced the endosome disruptive peptide with a fluorophore revealed that the >hundredfold difference in solubility between compounds such as Compound 31 and Compound 35 does not relate to an intrinsic difference in solubility between the cholesterylamine and cholesteryl carbamate, but rather is a specific property of these particular lipopeptide derivatives (data not shown). Additionally, cholesteryl carbamate Compound 33 lacking the Glu-Glu dipeptide sequence of Compound 34 was highly active and potent but exhibited low solubility in PBS (2 μM). Based on these results, we synthesized the alkyne-containing cholesterol carbamates Compounds 35-38. All of these compounds were highly potent, active, and soluble in PBS, with Compound 37 and Compound 38 exhibiting the highest potency ($IC_{50}$=40 nM). Studies of toxicity to Jurkat lymphocytes in culture after treatment for 48 hours revealed that potent and soluble endosome disruptors such as Compound 38 can exhibit >hundredfold selectivity for disruption of endosomes over toxicity to cells in culture.

We further synthesized and examined the properties of much shorter peptides lacking a cellular/endosomal-targeting lipid. Whereas the unconjugated PC4 peptide (Compound 39) was devoid of biological activity in the endosome disruption assay, replacement of the N-terminal SSA motif with UUU (Compound 41) conferred substantial endosome disruption activity (FIG. 2A-2C and Table 1). This activity was improved by incorporation of additional Aib residues (Compound 42) and substitution of Ala with Val at the C-terminus (compare Compound 43 with Compound 44). The substantial activity of peptide Compound 50 bearing only a single proline residue further demonstrates that a single residue capable of inducing a kink in the structure is sufficient to enable disruption of endosomes by these types of compounds. The studies of lipid conjugates indicate that these and related peptides could be used to promote endosomal escape of cargo when conjugated to a wide variety of cellular-targeting motifs.

FIGS. 2A-2C include dose-response curves for disruption of endosomes of Jurkat lymphocytes by synthetic compounds. Cells were treated with fluorescent molecular probe Compound 2 (2.5 μM) and endosome disruptors for 14 hours at 37° C. Enhanced cellular fluorescence resulting from release of the pH-sensitive fluorophore Compound 3 into the cytoplasm was quantified by flow cytometry.

Systems that integrate a cellular/endosomal-targeting motif, endosome disruptive element, and linked cargo could also be useful for delivery applications. To create examples of these types of systems, we investigated attachment of a fluorophore as model cargo though acylation of amine-containing side chains, as well as coupling via triazoles derived from Cu-catalyzed Huisgen 1,3-dipolar cycloaddition reactions of alkynes with azides. The integrated systems of Compounds 55-60 were prepared to examine the influence of linker length and structure on delivery of carboxyfluorescein. The structures of integrated delivery systems of Compounds 55-60 include a cholesteryl carbamate linked to both an endosome disruptive peptide and carboxyfluorescein as cargo.

Figure 5:
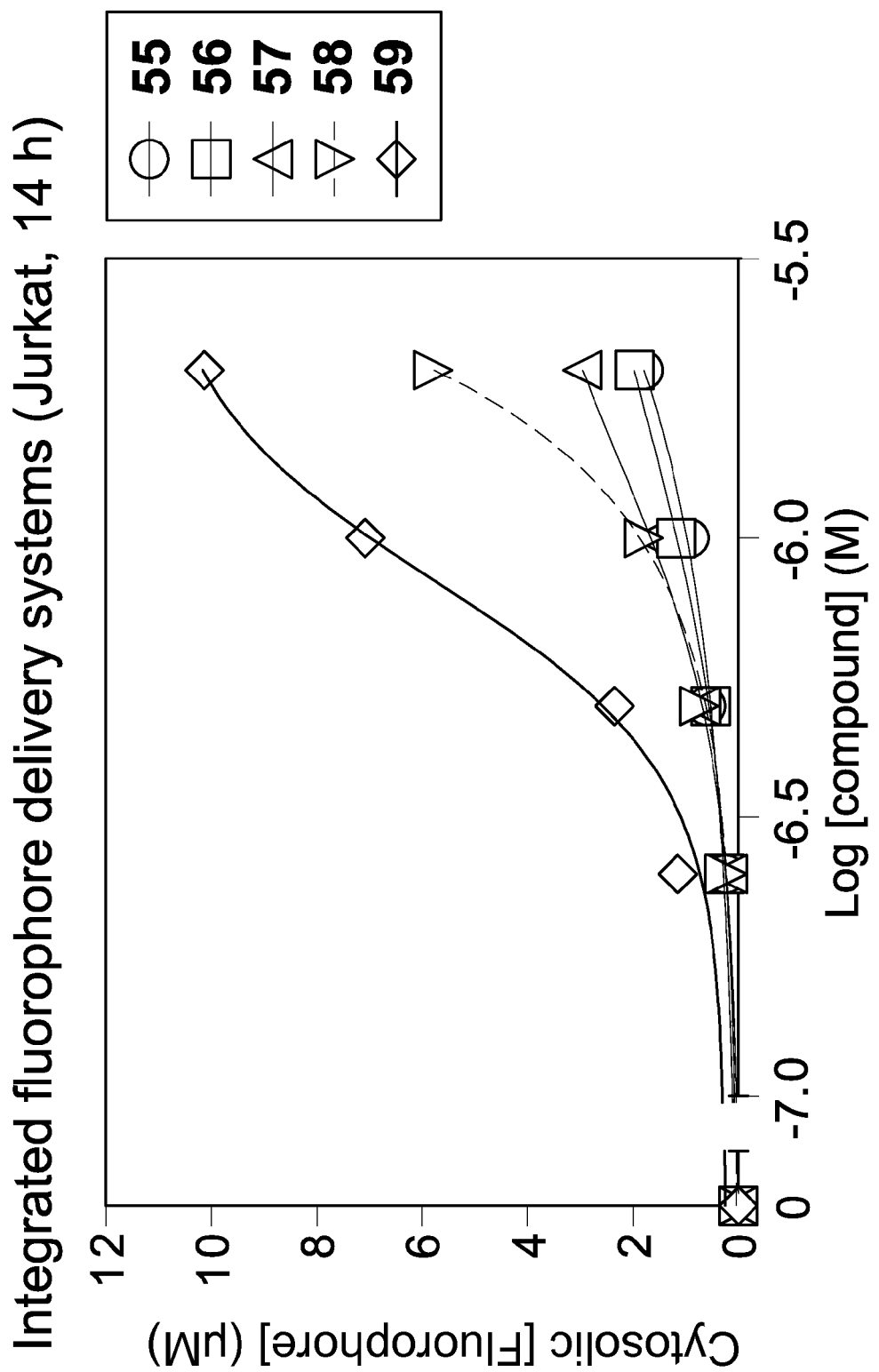
FIG. 5 includes a graph that shows endosomal release profiles of compounds of the invention.

Treatment of Jurkat lymphocytes with Compounds 55-60 resulted in dose-dependent accumulation of fluorescence in the cytosol (FIG. 5). By using bead standards (Spherotech) to convert cellular fluorescence to molecules of equivalent fluorescein (MEFL), and the diameter of Jurkat cells (12.3±0.7 μm by microscopy), the concentration of the fluorophore released into the cytosol was measured as a function of the concentration of the added delivery system. These systems were structurally specific, and small molecular changes to the linker between the cargo and peptide backbone strongly affected the efficiency of delivery. In particular, amine-containing side chains with three or fewer methylenes in the linker region (Compounds 55-57) were of relatively low potency/efficacy, but the four methylenes in the side chain of lysine provided modest potency/efficacy ($IC_{50}$~2.1 μM). In contrast, the triazole derivative Compound 59 was more than twice as potent ($IC_{50}$=830 nM). Moreover, treatment with 250 nM of Compound 59 yielded a cytosolic fluorophore concentration of over 1 μM, and at the maximum dose studied (2 μM), Compound 59 delivered 11 μM of the fluorophore into the cytosol after 14 h in culture.

FIG. 5 shows comparative efficacy of integrated fluorophore delivery systems. Dose-dependent accumulation of fluorophore Compound 3 in the cytosol of Jurkat lymphocytes after 14 h was determined by quantification of cellular fluorescence by flow cytometry, conversion to MEFL using bead standards, and calculation based on the average diameter of living Jurkat lymphocytes (12.3 μm).

Jurkat lymphocytes treated with the integrated fluorescent disulfide Compound 59 and the isosteric amide Compound 60 were imaged by confocal microscopy. As shown in FIGS. 4A-4B, only the disulfide Compound 59 released the fluorophore into the cytosol. The amide Compound 60 remained trapped in early endosomes. These results further confirm the importance of a disulfide or other cleavable linker between the delivery system and the cargo for release from endosomes by this mechanism.

FIGS. 4A-4B show confocal and DIC micrographs of living Jurkat lymphocytes treated for 16 h with the disulfide-linked fluorophore delivery system Compound 59 (Panel A) and the analogous amide control Compound 60 (Panel B). Scale bar=10 microns.

Figure 6:
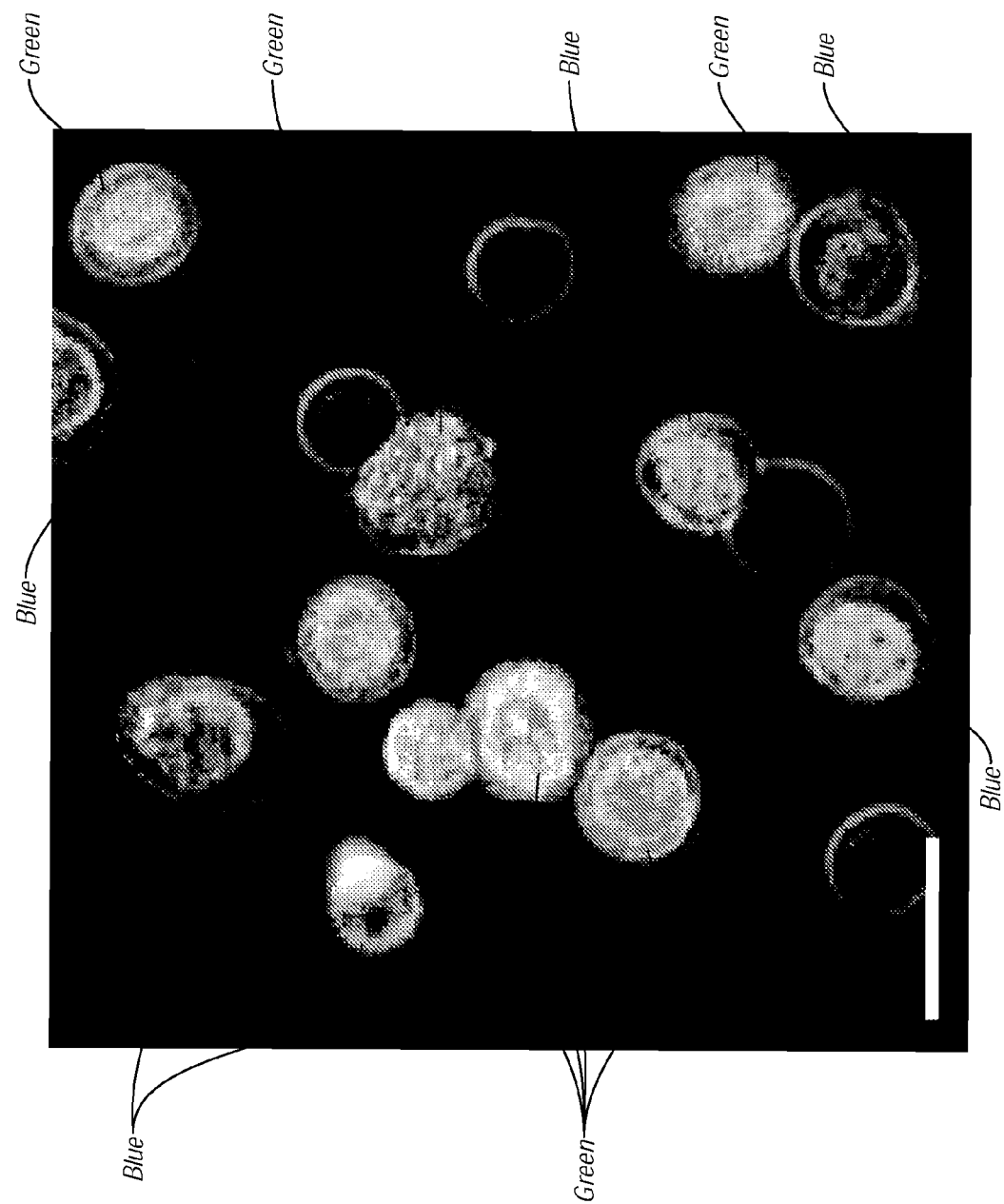
FIG. 6 includes a micrograph showing endosomal release obtained after treatment with Compound 59.

To examine the potential of these types of compounds in vivo, the integrated fluorescent disulfide Compound 59 was injected into the tail vein of B6D2F1 mice at 25 mg/Kg in 100 μL of 1:1 PBS:DMSO. After 8 hours, splenocytes were harvested and imaged by confocal microscopy. As shown in FIG. 6, green fluorescence was observed in the cytosol of living nucleated cells. These results suggest that these delivery systems have the potential for substantial half-lives and high stability in vivo.

FIG. 6 shows overlaid confocal fluorescence (blue/green) and DIC micrographs of living splenocytes isolated from B6D2F1 mice. Mice were subjected to tail vein injection of the disulfide-linked fluorophore delivery system Compound 59 at 25 mg/Kg. After 8 hours, cells were harvested by splenectomy and processing with a gentle max tissue dissociator. Cells were treated with blue fluorescent cell permeable Hoechst 33342 nuclear stain and red fluorescent cell-impermeable propidium iodide nuclear stain to identify cells suitable for analysis of the subcellular distribution of the green fluorescent probe. All of the cells shown in the field were living nucleated cells or erythrocytes as evidenced by positive Hoechst staining and lack of propidium iodide staining Erythrocytes are non-fluorescent. Scale bar=10 microns.

In one embodiment, the conformationally-constrained endosomal-disrupting peptide can include a general structure as in Formulae 1-1C, where CC-Peptide is the peptide or peptide sequence that adds a conformational constraint to the conformationally-constrained endosomal-disrupting peptide and ED-Peptide is the peptide or peptide sequence that provides for endosomal disruption. For example, the ED-Peptide includes an amino acid that induces a kink or disruption in peptide secondary structure, and can be referred to as ED-KP. The ED-KP is an endosomal-disrupting kinked peptide, which can be a modified PC4 peptide, which is an example of a kinked peptide.

In one embodiment, the conformationally-constrained endosomal-disrupting peptide can be included in a cargo delivery molecule having a cargo moiety and/or targeting moiety with a general structure as in Formulae 2-2C.

In one embodiment, the conformationally-constrained endosomal-disrupting peptide can be included in a cargo delivery molecule having one of a cargo moiety or targeting moiety with a general structure as in Formulae 3-3C and 4-4C.

Formula 1=CC-Peptide)$_{n1}$-(Peptide)$_{n2}$-(ED-KP)$_{n3}$-(Peptide)$_{n4}$.
Formula 1A=(CC-Peptide)$_{n1}$-(L1)$_{n2}$-(ED-KP)$_{n3}$-(L2)$_{n4}$.
Formula 1B=(CC-Peptide)$_{n1}$-(Xaa)$_{n2}$-(ED-KP)$_{n3}$-(Xaa)$_{n4}$.
Formula 1C=(CC-Peptide)$_{n1}$-(Xaa$^1$)$_{n2}$-(ED-KP)$_{n3}$-(Xaa$^2$)$_{n4}$.
Formula 2=Z$^1$-Y$^1$-X$^1$-(CC-Peptide)$_{n1}$-(Peptide)$_{n2}$-(ED-KP)$_{n3}$-(Peptide)$_{n4}$-X$^2$-Y$^2$-Z$^2$.
Formula 2A=Z$^1$-Y$^1$-X$^1$-(CC-Peptide)$_{n1}$-(L1)$_{n2}$-(ED-KP)$_{n3}$-(L2)$_{n4}$-X$^2$-Y$^2$-Z$^2$.
Formula 2B=Z$^1$-Y$^1$-X$^1$-(CC-Peptide)$_{n1}$-(Xaa)$_{n2}$-(ED-KP)$_{n3}$-(Xaa)$_{n4}$-X$^2$-Y$^2$-Z$^2$.
Formula 2C=Z$^1$-Y$^1$-X$^1$-(CC-Peptide)$_{n1}$-(Xaa$^1$)$_{n2}$-(ED-KP)$_{n3}$-(Xaa$^2$)$_{n4}$-X$^2$-Y$^2$-Z$^2$.
Formula 3=Z$^1$-Y$^1$-X$^1$-(CC-Peptide)$_{n1}$-(Peptide)$_{n2}$-(ED-KP)$_{n3}$-(Peptide)$_{n4}$.
Formula 3A=Z$^1$-Y$^1$-X$^1$-(CC-Peptide)$_{n1}$-(L1)$_{n2}$-(ED-KP)$_{n3}$-(L2)$_{n4}$.
Formula 3B=Z$^1$-Y$^1$-X$^1$-(CC-Peptide)$_{n1}$-(Xaa)$_{n2}$-(ED-KP)$_{n3}$-(Xaa)$_{n4}$.
Formula 3C=Z$^1$-Y$^1$-X$^1$-(CC-Peptide)$_{n1}$-(Xaa$^1$)$_{n2}$-(ED-KP)$_{n3}$-(Xaa$^2$)$_{n4}$.
Formula 4=(CC-Peptide)$_{n1}$-(Peptide)$_{n2}$-(ED-KP)$_{n3}$-(Peptide)$_{n4}$-X$^2$-Y$^2$-Z$^2$.
Formula 4A=(CC-Peptide)$_{n1}$-(L1)$_{n2}$-(ED-KP)$_{n3}$-(L2)$_{n4}$-X$^2$-Y$^2$-Z$^2$.
Formula 4B=(CC-Peptide)$_{n1}$-(Xaa)$_{n2}$-(ED-KP)$_{n3}$-(Xaa)$_{n4}$-X$^2$-Y$^2$-Z$^2$.
Formula 4C=(CC-Peptide)$_{n1}$-(Xaa$^1$)$_{n2}$-(ED-KP)$_{n3}$-(Xaa$^2$)$_{n4}$-X$^2$-Y$^2$-Z$^2$.

In one embodiment, the conformation-constraining peptide (i.e., CC-Peptide) is replaced with a conformation-constraining moiety (CCM) and the endosomal-disrupting peptide (i.e., ED-Peptide) is replaced with an endosomal-disrupting kinked peptide (ED-KP). In one embodiment, the conformationally-constrained endosomal-disrupting peptide can include a general structure as in Formulae 5-5C, where CCM is a chemical moiety that conformationally constrains the conformationally-constrained endosomal-disrupting peptide and KP is the kinked peptide that that provides for endosomal disruption. KP can be a kinked helix or other kinked peptide structure or has at least one amino acid that destabilizes or kinks a helix, or it can be a mimic of a kinked helix, any of which that has endosomal disrupting properties. In one embodiment, the conformationally-constrained endosomal-disrupting peptide can be included in a cargo delivery molecule having a cargo moiety and targeting moiety with a general structure as in Formulae 6-6C. In one embodiment, the conformationally-constrained endosomal-disrupting peptide can be included in a cargo delivery molecule having one of a cargo moiety or targeting moiety with a general structure as in Formulae 7-7C and 8-8C.

Formula 5=(CCM)$_{n1}$-(Peptide)$_{n2}$-(ED-KP)$_{n3}$-(Peptide)$_{n4}$.
Formula 5A=(CCM)$_{n1}$-(L1)$_{n2}$-(ED-KP)$_{n3}$-(L2)$_{n4}$.
Formula 5B=(CCM)$_{n1}$-(Xaa)$_{n2}$-(ED-KP)$_{n3}$-(Xaa)$_{n4}$.
Formula 5C=(CCM)$_{n1}$-(Xaa$^1$)$_{n2}$-(ED-KP)$_{n3}$-(Xaa$^2$)$_{n4}$.
Formula 6=Z$^1$-Y$^1$-X$^1$-(CCM)$_{n1}$-(Peptide)$_{n2}$-(ED-KP)$_{n3}$-(Peptide)$_{n4}$-X$^2$-Y$^2$-Z$^2$.
Formula 6A=Z$^1$-Y$^1$-X$^1$-(CCM)$_{n1}$-(L1)$_{n2}$-(ED-KP)$_{n3}$-(L2)$_{n4}$-X$^2$-Y$^2$-Z$^2$.
Formula 6B=Z$^1$-Y$^1$-X$^1$-(CCM)$_{n1}$-(Xaa)$_{n2}$-(ED-KP)$_{n3}$-(Xaa)$_{n4}$-X$^2$-Y$^2$-Z$^2$.
Formula 6C=Z$^1$-Y$^1$-X$^1$-(CCM)$_{n1}$-(Xaa$^1$)$_{n2}$-(ED-KP)$_{n3}$-(Xaa$^2$)$_{n4}$-X$^2$-Y$^2$-Z$^2$.
Formula 7=Z$^1$-Y$^1$-X$^1$-(CCM)$_{n1}$-(Peptide)$_{n2}$-(ED-KP)$_{n3}$-(Peptide)$_{n4}$.
Formula 7A=Z$^1$-Y$^1$-X$^1$-(CCM)$_{n1}$-(L1)$_{n2}$-(ED-KP)$_{n3}$-(L2)$_{n4}$.
Formula 7B=Z$^1$-Y$^1$-X$^1$-(CCM)$_{n1}$-(Xaa)$_{n2}$-(ED-KP)$_{n3}$-(Xaa)$_{n4}$.
Formula 7C=Z$^1$-Y$^1$-X$^1$-(CCM)$_{n1}$-(Xaa$^1$)$_{n2}$-(ED-KP)$_{n3}$-(Xaa$^2$)$_{n4}$.
Formula 8=(CCM)$_{n1}$-(Peptide)$_{n2}$-(ED-KP)$_{n3}$-(Peptide)$_{n4}$-X$^2$-Y$^2$-Z$^2$.
Formula 8A=(CCM)$_{n1}$-(L1)$_{n2}$-(ED-KP)$_{n3}$-(L2)$_{n4}$-X$^2$-Y$^2$-Z$^2$.
Formula 8B=(CCM)$_{n1}$-(Xaa)$_{n2}$-(ED-KP)$_{n3}$-(Xaa)$_{n4}$-X$^2$-Y$^2$-Z$^2$.
Formula 8C=(CCM)$_{n1}$-(Xaa$^1$)$_{n2}$-(ED-KP)$_{n3}$-(Xaa$^2$)$_{n4}$-X$^2$-Y$^2$-Z$^2$.

In one aspect, in any Formula, n1, n2, n3, n4, and n5 can be 0-50, such as 0, 1, 2, 3, 4, 5, 6, 7, 8, 9, 10, 15, 20, 25, 30, 35, 40, 45 or 50 or other integer value in this range.

In one aspect, Xaa, Xaa$^1$, and Xaa$^2$ can independently be one or more natural or non-natural amino acids, essential amino acids, or non-essential amino acids, or derivatives of amino acids having L or D configuration. X$^1$ or X$^2$ are independently nothing or a coupling group or beta-alanine residues or a polypeptide. Y$^1$ or Y$^2$ are independently nothing or a linker. Z$^1$ or Z$^2$ are independently an agent or cargo for delivery into a cell or a cell-targeting moiety for targeting a cell. The cell-targeting moiety can be a receptor-targeting moiety and/or a membrane-targeting moiety. Any amino acid can have L or D configuration.

In one embodiment, in the formulae shown, Z (e.g., Z$^1$ and/or Z$^2$) can be a targeting moiety, where Y (e.g., Y$^1$ or Y$^2$) or X (e.g., X$^1$ or X$^2$) includes a cargo moiety coupled thereto, such as shown in Compounds 55-60 and 70-72, and which can be represented by Formulae 2, 2A, 2B, 2C, 3, 3A, 3B, 3C, 4, 4A, 4B, 4C, 6, 6A, 6B, 6C, 7, 7A, 7B, 7C, 8, 8A, 8B, and/or 8C. The L (e.g., L1 or L2) may also include a cargo moiety coupled thereto, which can be represented by the same compounds.

In one embodiment, the cell-targeting moiety Z$^1$ and/or Z$^2$ is a cholesterol derivative selected from the group consisting of cholesterol, dihydrocholesterol, sitosterol, cholesteryl, dihydrocholesteryl, cholesterylamine, dihydrocholesterylamine, sitosterylamine, or derivative thereof. The cell-targeting moiety can be any moiety that targets and interacts with a receptor to facilitate RME. The cell-targeting moiety can be a molecule, protein, peptide, antibody, nucleic acid, carbohydrate, fragment thereof, or other.

In one embodiment, the linkers Y$^1$ or Y$^2$ are independently selected from a straight chain or branched or cyclic substituted or unsubstituted alkyl group having C1-C100 or an aromatic group, amino acid, a polypeptide, a polynucleotide, polysaccharide, a polyethylene glycol, a biodegradable linker, or combinations thereof. When substituted, the substituent can be a cargo molecule.

In one embodiment, the coupling groups X$^1$ or X$^2$ independently include an amide, ether, ester, carbamate, alkyl, aryl, alkene, triazole, amine, or alkanol. Alternatively, the coupling group can be derived from a coupling reaction between the linker and a coupling agent selected from a dithio diacid, a dicarboxylic acid, an acrylic moiety, a diazide, a styrene, a vinyl carboxylic acid, a urethane, a vinyl acetate, a vinyl ether, a Diels-Alder reagent, disulfides, hydrazones, imines, acetals, orthoesters, or other acid-labile or redox sensitive groups that allow release of agents in cells or tissues, photopolymerizable moiety, photocleavable moiety, derivatives thereof, and combinations thereof.

In one embodiment, the cargo molecule agents $Z^1$ or $Z^2$ are independently selected from therapeutic agents, imaging agents, diagnostic agents, assay agents, toxic agents, or combinations thereof. Examples of the agents $Z^1$ or $Z^2$ independently include a protein, peptide, polypeptide, nucleic acid, RNA, DNA, RNA/DNA hybrid, PNA, morpholinos, oligomers, siRNA, carbohydrates, lipids, markers, luminophores, tracer substances, molecular probes, oligopeptides, drugs, prodrug, toxins, a small molecule, a enzyme substrate, or combinations thereof.

In one embodiment, one of $Z^1$ or $Z^2$ is a targeting moiety and the other is cargo.

In one embodiment, the compound includes one or more beta-alanine residues in the Y (e.g., $Y^1$ or $Y^2$) linker between the X (e.g., $X^1$ or $X^2$) coupling group and the Z (e.g., $Z^1$ and/or $Z^2$) targeting moiety.

In one embodiment, the CC-Peptide is or includes one or more Aib moieties or a peptide having two or more Aib moieties that are in sequence or separate. In one embodiment, the CC-Peptide is or includes one or more alanine moieties or a peptide having one or more alanine moieties (e.g., beta-alanine) that are in sequence or separate. In one embodiment, the CC-Peptide is or includes other conformation-stabilizing or conformation-constraining amino acids or peptide sequences. In one aspect, the CC-Peptide can include one or more Aib moieties and/or one or more alanine moieties. Combinations of embodiments described above may also be used.

In one embodiment, the ED-KP is or includes one or more proline moieties or a peptide having two or more proline moieties that are in sequence or separate. In one example, the ED-KP includes two sequential proline moieties. In one aspect, the ED-KP is or includes one or more glycine moieties or a peptide having two or more glycine moieties that are in sequence or separate. In one example, the ED-KP includes two sequential glycine moieties. In one aspect, the ED-KP is or includes one or more glycine moieties and one or more proline moieties or a peptide having the glycine and proline are in sequence or separate. In one example, the ED-KP includes glycine-proline or proline-glycine moieties. In one embodiment, the ED-Peptide is or includes one or more secondary structure-altering amino acid moieties or a peptide having one or more secondary structure-altering amino acid moieties that are in sequence or separate. The ED-KP is a modified PC4 having a kink. Combinations of embodiments described above may also be used.

In one embodiment, the Peptide can be any aromatic, aliphatic, or other amino acids including non-natural aromatic, aliphatic, or other amino acids or derivatives thereof. These derivatives include but are not limited to N-alkyl amino acids. In one embodiment, the Peptide includes one or more Xaa, $Xaa^1$, or $Xaa^2$. In one embodiment, the Peptide can be a linker L1 or L2, which linker L1 or L2 can be a straight chain or branched or cyclic substituted or unsubstituted alkyl group having C1-C100 or an aromatic group, amino acid, a polypeptide, a polynucleotide, polysaccharide, a polyethylene glycol, a biodegradable linker, or combinations thereof In one embodiment, Xaa, $Xaa^1$, or $Xaa^2$ are independently phenylalanine, tryptophan, histidine, tyrosine, thyroxine, or other aromatic amino acid.

In one embodiment, the conformationally-constraining moiety (CCM) can be a conformation-stabilizing amino acid, conformation-stabilizing peptide, conformation-stabilizing functional group, conformation-stabilizing helix mimics, or conformation-constrained amino acids or conformation-constraining peptides. The endosomal-disrupting kinked peptide (ED-KP) can be a suitable peptide sequence or mimic thereof In one aspect, $X^1$, $Y^1$, and $Z^1$ and $X^2$, $Y^2$, and $Z^2$ independently can each represent nothing (unmodified), one or more functional groups, one or more amino acids, a capping group, a solubilizing group such as PEG or other motif that alters solubility, a linker to a targeting motif, or a targeting motif such as a targeting motif comprising a cellular-binding or membrane-binding moiety such as a small molecule, protein, peptide, lipid, antibody, cholesterol or a cholesterol mimic, carbohydrate, nucleic acid, or other moiety with affinity for cellular components or membranes. $X^1$, $Y^1$, and $Z^1$ and $X^2$, $Y^2$, and $Z^2$ can also represent zero, one, or more cargo molecules including nucleic acids, peptides, proteins, small molecules, drugs, or probes linked to the specific structure. $X^1$, $Y^1$, and $Z^1$ and $X^2$, $Y^2$, and $Z^2$ can also be independently defined for X, Y, and Z in the incorporated references. In one aspect, the targeting moiety can be a cholesterol or cholesterol derivative.

In one aspect, the CCM can be one or more 2-aminoisobutyric acid (i.e., Aib) moieties or a polypeptide containing one or more Aib. Also, CCM can include two or more Aib, which can be sequential Aib or an amino acid or peptide can be between the Aib moieties.

In one embodiment, each Aib moiety can be replaced by other helix-stabilizing amino acids (e.g., natural or non-natural), helix-stabilizing crosslinking groups, other helix-stabilizing modifications, or other conformationally-restricted amino acids or groups. Examples of these are found in the incorporated references or generally known to one of ordinary skill in the art. Specifically, helix-stabilizing amino acids include alanine and others as described in Richardson et al. "Amino Acid Preferences for Specific Locations at the Ends of Alpha Helices" Science 1988, 240, 1648-1652.

In one embodiment, the conformationally-constrained endosomal-disrupting peptide can include a general structure as in Formula 9, which provides a modified PC4 peptide, which is a kinked PC4 peptide derivative that is conformationally constrained in the kink. That is, the structure of Formula 9 includes kinked peptide portion and the conformationally-constraining peptide portion. In one embodiment, the conformationally-constrained endosomal-disrupting peptide can be included in a cargo delivery molecule having a cargo moiety and targeting moiety with a general structure as in Formula 10. In one embodiment, the conformationally-constrained endosomal-disrupting peptide can be included in a cargo delivery molecule having one of a targeting moiety or a cargo as in Formula 11 or Formula 12.

Formula 9=$(Aib)_{n1}$-$(Xaa^1)_{n2}$-$(KP)_{n3}$-$(Xaa^2)_{n4}$.
Formula 10=$Z^1$-$Y^1$-$X^1$-$(Aib)_{n1}$-$(Xaa^1)_{n2}$-$(KP)_{n3}$-$(Xaa^2)_{n4}$-$X^2$-$Y^2$-$Z^2$.
Formula 11=$Z^1$-$Y^1$-$X^1$-$(Aib)_{n1}$-$(Xaa^1)_{n2}$-$(KP)_{n3}$-$(Xaa^2)_{n4}$.
Formula 12=$(Aib)_{n1}$-$(Xaa^1)_{n2}$-$(KP)_{n3}$-$(Xaa^2)_{n4}$-$X^2$-$Y^2$-$Z^2$.

All of the variables are defined herein, with KP being a kinked peptide or an amino acid that causes a peptide to kink, such as one or more amino acids that cause an endosomal-disrupting peptide sequence to kink. As such, all or part of $(Xaa^1)_{n2}$ and/or $(Xaa^2)_{n3}$ provide for the endosomal-disrupting peptide or the endosomal-disrupting functionality. The $(KP)_{n3}$ provides the kink in the endosomal-disrupting peptide. The $(Aib)_{n1}$ provides the conformation constraint. The KP can be one or more prolines or one or more glycines or a combination of one or more prolines and one or more glycines. Examples include: proline-proline, proline-glycine, glycine-proline, and glycine-glycine, as well as tripeptides, tetrapeptides, or n-peptides thereof, where n is an integer.

In one aspect, the KP can be substituted with other secondary structure-altering moieties or amino acids. The KP can be replaced by other amino acids that alter secondary structure of peptides that may or may not be separated by one or more amino acids. In Formulae 9-9C, 10-10C, 11-11C, and 12-12C, KP1 can be the same or different from KP and $Xaa^3$ and/or $Xaa^4$ can be the same or different from $Xaa^1$ or $Xaa^2$. The n5 can be an integer that is the same or different from n3, and n6 can be an integer that is the same or different from n4. The n7 can be any integer as described for an "n" herein (e.g., is 0-50, such as 0, 1, 2, 3, 4, 5, 6, 7, 8, 9, 10, 15, 20, 25, 30, 35, 40, 45 or 50, or other value in this range.

Formula 9A=$(Aib)_{n1}$-$(Xaa^1)_{n2}$-$(KP)_{n3}$-$(Xaa^2)_{n4}$-$(KP1)_{n5}$.
Formula 10A=$Z^1$-$Y^1$-$X^1$-$(Aib)_{n1}$-$(Xaa^1)_{n2}$-$(KP)_{n3}$-$(Xaa^2)_{n4}$-$(KP1)_{n5}$-$X^2$-$Y^2$-$Z^2$.
Formula 11A=$Z^1$-$Y^1$-$X^1$-$(Aib)_{n1}$-$(Xaa^1)_{n2}$-$(KP)_{n3}$-$(Xaa^2)_{n4}$-$(KP1)_{n5}$.
Formula 12A=$(Aib)_{n1}$-$(Xaa^1)_{n2}$-$(KP)_{n3}$-$(Xaa^2)_{n4}$-$(KP1)_{n5}$-$X^2$-$Y^2$-$Z^2$.
Formula 9B=$(Aib)_{n1}$-$(Xaa^1)_{n2}$-$(KP)_{n3}$-$(Xaa^2)_{n4}$-$(KP1)_{n5}$-$(Xaa^3)_{n6}$.
Formula 10B=$Z^1$-$Y^1$-$X^1$-$(Aib)_{n1}$-$(Xaa^1)_{n2}$-$(KP)_{n3}$-$(Xaa^2)_{n4}$-$(KP1)_{n5}$-$(Xaa^3)_{n6}$-$X^2$-$Y^2$-$Z^2$.
Formula 11B=$Z^1$-$Y^1$-$X^1$-$(Aib)_{n1}$-$(Xaa^1)_{n2}$-$(KP)_{n3}$-$(Xaa^2)_{n4}$-$(KP1)_{n5}$-$(Xaa^3)_{n6}$.
Formula 12B=$(Aib)_{n1}$-$(Xaa^1)_{n2}$-$(KP)_{n3}$-$(Xaa^2)_{n4}$-$(KP1)_{n5}$-$(Xaa^3)_{n6}$-$X^2$-$Y^2$-$Z^2$.
Formula 9C=$(Xaa^4)_{n7}$-$(Aib)_{n1}$-$(Xaa^1)_{n2}$-$(KP)_{n3}$-$(Xaa^2)_{n4}$-$(KP1)_{n5}$.
Formula 10C=$Z^1$-$Y^1$-$X^1$-$(Xaa^4)_{n7}$-$(Aib)_{n1}$-$(Xaa^1)_{n2}$-$(KP)_{n3}$-$(Xaa^2)_{n4}$-$(KP1)_{n5}$-$X^2$-$Y^2$-$Z^2$.
Formula 11C=$Z^1$-$Y^1$-$X^1$-$(Xaa^4)_{n7}$-$(Aib)_{n1}$-$(Xaa^1)_{n2}$-$(KP)_{n3}$-$(Xaa^2)_{n4}$-$(KP1)_{n5}$.
Formula 12C=$(Xaa^4)_{n7}$-$(Aib)_{n1}$-$(Xaa^1)_{n2}$-$(KP)_{n3}$-$(Xaa^2)_{n4}$-$(KP1)_{n5}$-$X^2$-$Y^2$-$Z^2$.

The X, Y, and Z moieties of the formulae can represent nothing (unmodified), one or more functional groups, one or more amino acids, a capping group, a solubilizing group such as PEG or other motif that alters solubility, a linker to a targeting motif, or a targeting motif comprising a cellular-binding or membrane-binding moiety such as a small molecule, protein, peptide, antibody, lipid, cholesterol or a cholesterol mimic, carbohydrate, nucleic acid, or other moiety with affinity for cellular components or membranes. X, Y, and Z moieties of the formulae can also represent zero, one, or more cargo molecules including nucleic acids, peptides, proteins, small molecules, drugs, toxins, enzyme substrates, or probes linked to the specific structure. The Xaa can be one or more aromatic, aliphatic, or other amino acids including non-natural aromatic, aliphatic, or other amino acids or derivatives thereof. Any of the "n" or monomers (e.g., n1, n2, n3, n4, n5, n6, etc.) can be n=0 to 50, 0 to 30, 0 to 20, 0 to 10, 0 to 5, or 0 to 2.

In one embodiment, Aib can be replaced by other helix-stabilizing amino acids (natural or non-natural), helix-stabilizing crosslinking groups, other helix-stabilizing modifications, or other conformationally-restricted amino acids or groups.

In one embodiment, the C-terminus can be modified such as by amidation or be unmodified.

In one embodiment, the linker (e.g., L or Y) can comprise amino acids or other coupling groups.

In one embodiment, the Pro in the ED-KP or KP can be replaced by other amino acids such as glycine that create a kink in a helix including two or more prolines or glycines or other amino acids or groups that alter secondary structure of peptides and that may or may not be separated by one or more amino acids. The incorporated references include examples.

In one embodiment, the Xaa is at least one amino acid that is either a natural aromatic amino acid (such as Tyr, Trp, or Phe) or a non-natural aromatic amino acid or mimic thereof.

In one embodiment, the conformationally-constrained endosomal-disrupting peptide can be included in a longer peptide sequence. Which longer peptide sequence is capable of being cleaved in a cell to form the conformationally-constrained endosomal-disrupting peptide of Formulae 1-1C, 5-5C, and 9-9C. That is, the Formulae of 1-1C, 5-5C, and 9-9C can be contained in a longer sequence that is cleaved in an endosome to form Formulae 1-1C, 5-5C, and 9-9C. The longer peptide sequence can also be included in the molecules that have targeting moieties and/or cargo. The cleaving of the longer peptide sequence can be by proteolysis. The proteolysis can be cell-specific, so that the endosome of specific cell types can be targeted for endosomal release.

In one embodiment, the targeting motif can be a lipid other than cholesterol or cholesterol derivative. In one embodiment, the targeting motif is a protein-binding small molecule (e.g., folic acid), peptide, protein, polypeptide, antibody, antibody fragment, or other protein-binding motif. The targeting motif can be receptor active and bind with cell surface receptors or other cellular biomolecules that undergo endocytosis.

The cargo can be any therapeutics, probes, or other cargo to be delivered into a cell. As such, the present invention can include the use of these agents for delivery of therapeutics, probes, or other cargo into a cell. The method can use these agents for assays or diagnostic purposes by delivering assay or diagnostic cargo into a cell. In one embodiment, the cargo (e.g., Z) can be covalently linked to the conformationally-constrained kinked peptide. In one embodiment, the cargo can be non-covalently linked with the conformationally-constrained kinked peptide.

In one embodiment, the present invention includes a conformationally-constrained endosomal-disrupting peptide that is a derivative of dodecapeptide PC4. The conformationally-constrained endosomal-disrupting peptide can be longer or shorter than PC4, and can have various amino acid substitutions, additions, deletions, or other modifications from PC4 so long as the conformationally-constrained endosomal-disrupting peptide is conformationally constrained and has the kink features. The PC4 derivative can be kinked and conformationally constrained in the kinked conformation.

By exhibiting unique structural features, the compounds of this invention are structurally different from previously reported endosome-disrupting agents and are substantially more potent and more active than previously reported agents, as shown by the data. It is indeed surprising and unexpected that conformationally-constrained kinked peptides can be more active in endosomal disruption from native or conformation-free peptides. Thus, the conformationally-constrained endosomal-disrupting peptides of the present invention are a significant advance in the art of endosomal disruption and cargo delivery platforms.

In the structures of Compounds 1 and 5-69, the peptide sequences shown can fit into any of the formulae shown herein. For example, the left side of sequences of Compounds 40-54 can be $(Aib)_{n1}$. The left side of sequences of Compounds 40-54 can be $(Xaa)_{n4}$. The PP can be the KP or KP1. The portion between the $(Aib)_{n1}$ and PP can be the $(Xaa)_{n2}$. The left side portions in sequences of Compounds 1 and 5-69 that include one or more U moieties can be the CC-Peptide and/or CCM. The right side portions to the right of any proline and/or glycine can be the right side amino acid sequence, such as Xaa, $Xaa^2$, and/or $Xaa^3$ or Peptide or L2. The portions having or being the prolines can be the ED-KP or KP or KP1. The portions between the U moieties and the prolines can be the Xaa or $Xaa^1$ or $L^1$ or Peptide.

In one embodiment, the sequences or structures of Compounds 1, 5-38, and 40-69 can include a different targeting moiety and/or the amide can be linked to a cargo. In another embodiment, the sequences or structures of Compounds 1, 5-38, and 40-69 can include the amino acid sequence shown with $X^1$, $Y^1$, and $Z^1$ at one end, and/or $X^2$, $Y^2$, and $Z^2$ at the other end.

In one embodiment, the molecule of the invention can include the Formula 13=A-Y-(Helix-Stabilizing Amino Acids, functional groups, helix mimics, or conformationally-constrained amino acids or groups)$_n$-(Xaa)$_n$-(Helix-Disrupting Amino Acids or groups or mimics)$_n$-(Xaa)$_n$-Z-B. In one embodiment, the molecule of the invention can include the Formula 14=A-Y-(Aib)$_n$-(Xaa)$_n$-(Pro or other secondary structure-altering amino acid)$_n$-(Xaa)$_n$-Z-B. Where A, B, Y, and Z can represent nothing (unmodified), one or more functional groups, one or more amino acids, a capping group, a solubilizing group such as PEG or other motif that alters solubility, a linker to a targeting motif, or a targeting motif comprising a cellular-binding or membrane-binding moiety such as a small molecule, protein, peptide, lipid, cholesterol or a cholesterol mimic, carbohydrate, nucleic acid, or other moiety with affinity for cellular components or membranes. A, B, Y, or Z can also represent zero, one, or more cargo molecules including nucleic acids, peptides, proteins, small molecules, drugs, toxins, enzyme substrates, or probes linked to the specific structure. Xaa is one or more aromatic, aliphatic, or other amino acids including non-natural aromatic, aliphatic, or other amino acids or derivatives thereof. The n is from 0 to 50, or any specific integer therebetween. The Aib can be replaced by other helix-stabilizing amino acids (natural or non-natural), helix-stabilizing crosslinking groups, other helix-stabilizing modifications, or other conformationally-restricted amino acids or groups. The C-terminus can be modified such as by amidation or unmodified. The linker can comprise amino acids or other coupling groups. The Pro can be replaced by other amino acids such as glycine, thiaproline, or analogues or derivatives of proline or glycine or other amino acids that create a kink in a helix including two or more prolines or glycines or other amino acids or groups that alter the structure of peptides by kinking a helix or inducing a turn or bend and that may or may not be separated by one or more amino acids. In one aspect, at least one amino acid of Xaa is either a natural aromatic amino acid (such as Tyr, Trp, or Phe) or a non-natural aromatic amino acid or mimic. In one aspect, the active membrane-disruptive peptide is generated by proteolysis of a longer peptide sequence.

Pharmaceutical compositions can include the compounds of the invention, and can include, without limitation, lyophilized powders or aqueous or non-aqueous sterile injectable solutions or suspensions, which may further contain antioxidants, buffers, bacteriostats, and solutes that render the compositions substantially compatible with the tissues or the blood of an intended recipient. Other components that may be present in such compositions include water, surfactants (e.g., Tween®), alcohols, polyols, glycerin, and vegetable oils, for example. Extemporaneous injection solutions and suspensions may be prepared from sterile powders, granules, tablets, or concentrated solutions or suspensions. The composition may be supplied, for example, but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesyl-phosphotidyl-ethanolamine (DOPE), and liposomes. Such compositions should contain a therapeutically effective amount of the compound, together with a suitable amount of carrier so as to provide the form for direct administration to the patient.

The compositions described herein can be administered, for example, by parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Common carriers or excipients can be used for preparing pharmaceutical compositions designed for such routes of administration.

In one embodiment, a conformationally-constrained kinked peptide comprises: a conformationally-constraining portion and a kinked portion linked to the conformationally-constraining portion that conformationally constrains the kinked portion, the kinked portion comprising an endosomal-disrupting peptide. The peptide can include a peptide sequence of one of SEQ ID NOs: 1, 5-38, or 40-54 and 61-69. In one aspect, the conformationally-constrained kinked portion is a majority portion of the peptide. In one aspect, the conformationally-constrained kinked portion is a minority portion of the peptide. In one aspect, the peptide can include one of Formulae 1-1C, wherein: CC-Peptide includes a peptide that conformationally constrains the ED-KP; Peptide independently includes natural, unnatural, essential or non-essential aromatic or aliphatic amino acids, or derivatives thereof having L or D configuration; ED-KP includes an endosomal-disrupting kinked peptide; Xaa, $Xaa^1$, and $Xaa^2$ are independently one or more natural or non-natural amino acids, essential amino acids, or non-essential amino acids, or derivatives of amino acids having L or D configuration; L1 and L2 are independently linkers; and n1, n2, n3, and n4 are independently 0-50.

In one embodiment, the peptide can include one of Formulae 5-5C, wherein: CCM includes a moiety that conformationally constrains the ED-KP; Peptide independently includes natural, unnatural, essential or non-essential aromatic, aliphatic, or other amino acids, or derivatives thereof having L or D configuration; ED-KP includes an endosomal-disrupting kinked peptide; Xaa, $Xaa^1$, and $Xaa^2$ are independently one or more natural or non-natural amino acids, essential amino acids, or non-essential amino acids, or derivatives of amino acids having L or D configuration; L1 and L2 are independently linkers; and n1, n2, n3, and n4 are independently 0-50.

In one embodiment, the peptide can include one of Formulae 9-9C, wherein: KP and KP1 independently include a kinked peptide or an amino acid that causes peptide to kink; Xaa, Xaa$^1$, and Xaa$^2$ are independently one or more natural or non-natural amino acids, essential amino acids, or non-essential amino acids, or derivatives of amino acids having L or D configuration; and n1, n2, n3, n4, n5, n6, and n7 are independently 0-50.

In one embodiment, the peptide can include one of the peptide sequences of one of the SEQ ID NOs: 40-54 or 69.

In one embodiment, a cell-targeting compound can include: one or more of the peptides; and a targeting moiety linked to an end of the peptide.

In one embodiment, a cell-targeting compound can include the targeting moiety on the C-terminus or N-terminus of the peptide of one of SEQ ID NOs: 1, 5-38, or 40-54 and 6169.

In one embodiment, the cell-targeting compound can include one of Formulae 2-2C, 3-3C, or 4-4C, wherein: CC-Peptide includes a peptide that conformationally constrains the ED-KP; Peptide independently includes natural, unnatural, essential or non-essential aromatic or aliphatic amino acids, or derivatives thereof having L or D configuration; ED-KP includes an endosomal-disrupting kinked peptide; Xaa, Xaa$^1$, and Xaa$^2$ are independently one or more natural or non-natural amino acids, essential amino acids, or non-essential amino acids, or derivatives of amino acids having L or D configuration; L1 and L2 are independently linkers; n1, n2, n3, and n4 are independently 0-50; Z$^1$ and Z$^2$ are independently a targeting moiety, cargo moiety, or nothing, wherein at least one is a targeting moiety; Y$^1$ and Y$^2$ are independently nothing or a linker, or a linker having a cargo moiety; and X$^1$ and X$^2$ are independently nothing, a coupling group, one or more beta-alanine residues, or a polypeptide.

In one embodiment, the cell-targeting compound can include one of Formulae 6-6C, 7-7C, or 8-8C, wherein: CCM includes a moiety that conformationally constrains the ED-KP; Peptide independently includes natural, unnatural, essential or non-essential aromatic or aliphatic amino acids, or derivatives thereof having L or D configuration; ED-KP includes an endosomal-disrupting kinked peptide; Xaa, Xaa$^1$, and Xaa$^2$ are independently one or more natural or non-natural amino acids, essential amino acids, or non-essential amino acids, or derivatives of amino acids having L or D configuration; L1 and L2 are independently linkers; n1, n2, n3, and n4 are independently 0-50; Z$^1$ and Z$^2$ are independently a targeting moiety, cargo moiety, or nothing, wherein at least one is a targeting moiety; Y$^1$ and Y$^2$ are independently nothing or a linker, or a linker having a cargo moiety; and X$^1$ and X$^2$ are independently nothing, a coupling group, one or more beta-alanine residues, or a polypeptide.

In one embodiment, the cell-targeting compound includes a linker between and linking the one or more peptides and the targeting moiety. In one aspect, the linker is adjacent to a cargo moiety opposite of the cholesterol carbamate, wherein the cargo moiety is branched from the linker, wherein the linker includes a bi-glutamic acid adjacent to the branch having the cargo moiety.

In one embodiment, the cell-targeting compound includes one of Formulae 10-10C, 11-11C, or 12-1C wherein: KP and KP1 independently includes a kinked peptide or an amino acid that causes peptide to kink; Xaa, Xaa$^1$, and Xaa$^2$ are independently one or more natural or non-natural amino acids, essential amino acids, or non-essential amino acids, or derivatives of amino acids having L or D configuration; Z$^1$ and Z$^2$ are independently a targeting moiety, cargo moiety, or nothing, wherein at least one is a targeting moiety; Y$^1$ and Y$^2$ are independently nothing or a linker, or a linker having a cargo moiety; X$^1$ and X$^2$ are independently nothing, a coupling group, one or more beta-alanine residues, or a polypeptide; and n1, n2, n3, n4, n5, n6, and n7 are independently 0-50.

In one embodiment, the cell-targeting compound includes a structure of one of Compounds 1, 5-38, and 40-73.

In one embodiment, a cargo delivery compound includes: one of the peptides described herein; and a cargo moiety linked to the peptide.

In one embodiment, a cargo delivery molecule can include cargo that is a therapeutic agent, pharmaceutical, nutraceutical, diagnostic agent, assay agent, tracking agent, suicide agent, toxin, or any other agent.

In one embodiment, a molecule can include one or more beta-alanine residues between the peptide and the targeting moiety.

In one embodiment, a molecule can include the conformationally-constraining portion having one or more Aib moieties or a peptide having two or more Aib moieties that are in sequence or separate. In one aspect, the conformationally-constraining portion includes one or more alanine moieties or a peptide having one or more alanine moieties that are in sequence or separate. In one aspect, the kinked portion is or includes one or more proline moieties or a peptide having two or more proline moieties that are in sequence or separate. In one aspect, the kinked portion includes two sequential proline moieties. In one aspect, the kinked portion includes one or more glycine moieties or a peptide having two or more glycine moieties that are in sequence or separate. In one aspect, the kinked portion includes two sequential glycine moieties. In one aspect, the kinked portion includes one or more glycine moieties and one or more proline moieties or a peptide where the glycine and proline are in sequence or separate. In one aspect, the kinked portion includes one or more glycine-proline segments or one or more proline-glycine segments. In one aspect, Xaa, Xaa$^1$, or Xaa$^2$ are independently phenylalanine, tryptophan, histidine, tyrosine, thyroxine, or other aromatic amino acid.

In one embodiment, X$^1$, Y$^1$, and Z$^1$ and X$^2$, Y$^2$, and Z$^2$ independently can each represent nothing (unmodified), one or more functional groups, one or more amino acids, a capping group, a solubilizing group such as PEG or other motif that alters solubility, a linker to a targeting motif, or a targeting motif such as a targeting motif comprising a cellular-binding or membrane-binding moiety such as a small molecule, protein, peptide, lipid, cholesterol or a cholesterol mimic, carbohydrate, nucleic acid, or other moiety with affinity for cellular components or membranes. In one aspect, X$^1$, Y$^1$, and Z$^1$ and X$^2$, Y$^2$, and Z$^2$ represent zero, one, or more cargo molecules including nucleic acids, peptides, proteins, small molecules, drugs, or probes.

In one embodiment, the CCM can be one or more 2-aminoisobutyric acid (i.e., Aib) moieties or a polypeptide containing one or more Aib. In one aspect, CCM can include two or more Aib, which can be sequential Aib or an amino acid or peptide can be between the Aib moieties. In one aspect, each Aib moiety can be replaced by other helix-stabilizing amino acids (e.g., natural or non-natural), helix-stabilizing crosslinking groups, other helix-stabilizing modifications, or other conformationally-restricted amino acids or groups.

In one aspect, the coupling agent, such as $X^1$ and/or $X^2$ can be selected from a dithio diacid, a dicarboxylic acid, an acrylic moiety, a diazide, a styrene, a vinyl carboxylic acid, a urethane, a vinyl acetate, a vinyl ether, a Diels-Alder reagent, disulfides, hydrazones, imines, acetals, orthoesters, or other acid-labile or redox sensitive groups that allow release of agents in cells or tissues, photopolymerizable moiety, photocleavable moiety, derivatives thereof, and combinations thereof.

In one aspect, the invention includes a method of disrupting endosomes comprising: providing the molecule of the invention having an endosomal-disrupting peptide; and administering the molecule to a cell. In one aspect, the cell is in a cell culture. In one aspect, the cell is in a living organism. In one aspect, the method can include administering a sufficient amount of the molecule to disrupt the endosome of the cell.

In one embodiment, a method of delivering cargo to a cell can include: performing the method of disrupting endosomes of one of the embodiments with the molecule having a cargo moiety; and allowing the molecule and/or cargo to escape the endosome into cytoplasm of the cell.

In one embodiment, a method of targeting a cell for delivery of cargo can include: performing the method of disrupting endosomes with a molecule having a targeting moiety; and allowing the molecule to target and associate with a cell membrane sufficiently for endocytosis of the molecule.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety: PCT Publication WO 2011/019942; U.S. Publication 2010/0041773; α-Helix Stabilization by Natural and Unnatural Amino Acids with Alkyl Side Chains; PC Lyu et al.; *Proc. Natl. Aca. Sci USA*; Vol. 88, pp. 5317-5320, June 1991; An All-Hydrocarbon Cross-Linking System for Enhancing the Helicity and Metabolic Stability of Peptides; CE Schafmeister et al.; *J Am Chem Soc*; Vol. 122, pp. 5891-5892, 2000; Factors Governing Helical Preference of Peptides Containing Multiple α,α-dialkyl Amino Acids; G R Marshall et al.; *Proc Natl Acad Sci USA*; Vol. 87, pp. 487-491, January 1990; Helix Propensities of the Amino Acids Measured in Alanine-Based Peptides without Helix-Stabilizing Side-Chain Interactions; A Chakrabartty et al.; *Protein Science*; Vol. 3, pp. 843-852, 1994; NMR Structures of a Viral Peptide Inserted in Artificial Membranes; M Galloux et al.; *The Journal of Biological Chemistry*; Vol. 285, No. 25, pp. 19409-19421 Jun. 18, 2010; Amino Acid Preferences for Specific Locations at the Ends of a Helices; J S Richardson et al.; *Science*; Vol. 240, pp. 1648-1652, Jun. 17, 1988; Structural and Functional Implications of a Proline Residue in the Antimicrobial Peptide Gaegurin; J Y Suh; *Eur J Biochem*; Vol. 266, pp. 665-674, 1999; Using an Azobenzene Cross-Linker to Either Increase or Decrease Peptide Helix Content upon Trans-to-Cis Photoisomerization; DG Flint; *Chemistry & Biology*; Vol. 9, pp. 391-397, March 2002; *Endocytic Delivery of Vancomycin Mediated by a Synthetic Cell Surface Receptor: Rescue of Bacterially Infected Mammalian Cells and Tissue Targeting In Vivo*; S Boonyarattanakalin et al.; *J American Chemical Society*; Vol. 129, pp. 268-269, 2007; Selective Disruption of Early/Recycling Endosomes: Release of Disulfide-Linked Cargo Mediated by an N-Alkyl-3β-Cholesterylamine-Capped Peptide; Q Sun et al.; *J American Chemical Society*; Vol. 130, pp. 10064-10065, 2008.

The invention claimed is:

1. A cell-targeting compound comprising:
one or more of the peptides having a conformationally-constraining portion, and a kinked portion linked through a peptide linker to the conformationally-constraining portion that conformationally constrains the kinked portion, the kinked portion, peptide linker and conformationally-constraining portion includes one of SEQ ID NOs: 5-38, 40-54 or 61-69; and
a targeting moiety linked to an end of the peptide, wherein:
the kinked portion has an amino acid sequence that includes one or more amino acids independently selected from proline and glycine;
the conformationally-constrained portion includes one or more 2-aminoisobutyric acid residues; and
the peptide linker includes one or more natural or non-natural amino acids, essential amino acids, or non-essential amino acids, or amino acids having L or D configuration or peptide thereof.

2. The cell-targeting compound of claim 1, wherein the targeting moiety is on the C-terminus of the peptide.

3. The cell-targeting compound of claim 1, wherein the targeting moiety is on the N-terminus of the peptide.

4. The cell-targeting compound of claim 1, comprising one of Formulae 2-2C, 3-3C, or 4-4C, wherein:
ED-KP is the endosomal-disrupting kinked peptide having one or more amino acids independently selected from proline and glycine;
CC-Peptide includes a peptide having one or more 2-aminoisobutyric acid residues that conformationally-constrains the ED-KP;
Peptide independently includes natural, unnatural, essential or non-essential aromatic, aliphatic, or other amino acids, or having L or D configuration;
Xaa, $Xaa^1$, and $Xaa^2$ are independently one or more natural or non-natural amino acids, essential amino acids, or non-essential amino acids, or amino acids having L or D configuration;
L1 and L2 are independently linkers;
n1 and n3 are independently an integer greater than 0 and less than 50;
n2 and n4 are independently 0-50;
$Z^1$ and $Z^2$ are independently a targeting moiety, cargo moiety, or nothing, wherein at least one is a targeting moiety;
$Y^1$ and $Y^2$ are independently nothing or a linker, or a linker having a cargo moiety; and
$X^1$ and $X^2$ are independently nothing, a coupling group, one or more beta-alanine residues, or a polypeptide,
Formula $2=Z^1-Y^1-X^1$-(CC-Peptide)$_{n1}$-(Peptide)$_{n2}$-(ED-KP)$_{n3}$-(Peptide)$_{n4}$-$X^2$-$Y^2$-$Z^2$;
Formula $2A=Z^1-Y^1-X^1$-(CC-Peptide)$_{n1}$-(L1)$_{n2}$-(ED-KP)$_{n3}$-(L2)$_{n4}$-$X^2$-$Y^2$-$Z^2$;
Formula $2B=Z^1-Y^1-X^1$-(CC-Peptide)$_{n1}$-(Xaa)$_{n2}$-(ED-KP)$_{n3}$-(Xaa)$_{n4}$-$X^2$-$Y^2$-$Z^2$;
Formula $2C=Z^1-Y^1-X^1$-(CC-Peptide)$_{n1}$-(Xaa$^1$)$_{n2}$-(ED-KP)$_{n3}$-(Xaa$^2$)$_{n4}$-$X^2$-$Y^2$-$Z^2$;
Formula $3=Z^1-Y^1-X^1$-(CC-Peptide)$_{n1}$-(Peptide)$_{n2}$-(ED-KP)$_{n3}$-(Peptide)$_{n4}$;
Formula $3A=Z^1-Y^1-X^1$-(CC-Peptide)$_{n1}$-(L1)$_{n2}$-(ED-KP)$_{n3}$-(L2)$_{n4}$;
Formula $3B=Z^1-Y^1-X^1$-(CC-Peptide)$_{n1}$-(Xaa)$_{n2}$-(ED-KP)$_{n3}$-(Xaa)$_{n4}$;
Formula $3C=Z^1-Y^1-X^1$-(CC-Peptide)$_{n1}$-(Xaa$^1$)$_{n2}$-(ED-KP)$_{n3}$-(Xaa$^2$)$_{n4}$;
Formula $4=$(CC-Peptide)$_{n1}$-(Peptide)$_{n2}$-(ED-KP)$_{n3}$-(Peptide)$_{n4}$-$X^2$-$Y^2$-$Z^2$;
Formula $4A=$(CC-Peptide)$_{n1}$-(L1)$_{n2}$-(ED-KP)$_{n3}$-(L2)$_{n4}$-$X^2$-$Y^2$-$Z^2$;
Formula $4B=$(CC-Peptide)$_{n1}$-(Xaa)$_{n2}$-(ED-KP)$_{n3}$-(Xaa)$_{n4}$-$X^2$-$Y^2$-$Z^2$; and
Formula $4C=$(CC-Peptide)$_{n1}$-(Xaa$^1$)$_{n2}$-(ED-KP)$_{n3}$-(Xaa$^2$)$_{n4}$-$X^2$-$Y^2$-$Z^2$.

5. The cell-targeting compound of claim 1, comprising one of Formulae 6-6C, 7-7C, or 8-8C, wherein:
ED-KP is the endosomal-disrupting kinked peptide having one or more amino acids independently selected from proline and glycine;
CCM includes a moiety having one or more 2-aminoisobutyric acid residues that conformationally constrains the ED-KP;
Peptide independently includes natural, unnatural, essential or non-essential aromatic, aliphatic, or other amino acids, or having L or D configuration;
Xaa, $Xaa^1$, and $Xaa^2$ are independently one or more natural or non-natural amino acids, essential amino acids, or non-essential amino acids, or amino acids having L or D configuration;
L1 and L2 are independently linkers;
n1 and n3 are independently an integer greater than 0 and less than 50;
n2 and n4 are independently 0-50;
$Z^1$ and $Z^2$ are independently a targeting moiety, cargo moiety, or nothing, wherein at least one is a targeting moiety;
$Y^1$ and $Y^2$ are independently nothing or a linker, or a linker having a cargo moiety; and
$X^1$ and $X^2$ are independently nothing, a coupling group, one or more beta-alanine residues, or a polypeptide,
Formula $6=Z^1-Y^1-X^1$-(CCM)$_{n1}$-(Peptide)$_{n2}$-(ED-KP)$_{n3}$-(Peptide)$_{n4}$-$X^2$-$Y^2$-$Z^2$;
Formula $6A=Z^1-Y^1-X^1$-(CCM)$_{n1}$-(L1)$_{n2}$-(ED-KP)$_{n3}$-(L2)$_{n4}$-$X^2$-$Y^2$-$Z^2$;
Formula $6B=Z^1-Y^1-X^1$-(CCM)$_{n1}$-(Xaa)$_{n2}$-(ED-KP)$_{n3}$-(Xaa)$_{n4}$-$X^2$-$Y^2$-$Z^2$;
Formula $6C=Z^1-Y^1-X^1$-(CCM)$_{n1}$-(Xaa$^1$)$_{n2}$-(ED-KP)$_{n3}$-(Xaa$^2$)$_{n4}$-$X^2$-$Y^2$-$Z^2$;
Formula $7=Z^1-Y^1-X^1$-(CCM)$_{n1}$-(Peptide)$_{n2}$-(ED-KP)$_{n3}$-(Peptide)$_{n4}$;
Formula $7A=Z^1-Y^1-X^1$-(CCM)$_{n1}$-(L1)$_{n2}$-(ED-KP)$_{n3}$-(L2)$_{n4}$;
Formula $7B=Z^1-Y^1-X^1$-(CCM)$_{n1}$-(Xaa)$_{n2}$-(ED-KP)$_{n3}$-(Xaa)$_{n4}$;
Formula $7C=Z^1-Y^1-X^1$-(CCM)$_{n1}$-(Xaa$^1$)$_{n2}$-(ED-KP)$_{n3}$-(Xaa$^2$)$_{n4}$;
Formula $8=$(CCM)$_{n1}$-(Peptide)$_{n2}$-(ED-KP)$_{n3}$-(Peptide)$_{n4}$-$X^2$-$Y^2$-$Z^2$;
Formula $8A=$(CCM)$_{n1}$-(L1)$_{n2}$-(ED-KP)$_{n3}$-(L2)$_{n4}$-$X^2$-$Y^2$-$Z^2$;
Formula $8B=$(CCM)$_{n1}$-(Xaa)$_{n2}$-(ED-KP)$_{n3}$-(Xaa)$_{n4}$-$X^2$-$Y^2$-$Z^2$; and
Formula $8C=$(CCM)$_{n1}$-(Xaa$^1$)$_{n2}$-(ED-KP)$_{n3}$-(Xaa$^2$)$_{n4}$-$X^2$-$Y^2$-$Z^2$.

6. The cell-targeting compound of claim 1, comprising one of Formulae 10-10C, 11-11C, or 12-12C wherein:
KP and KP1 one or more amino acids independently selected from proline and glycine that can cause the endosomal-disrupting kinked peptide to kink;
Aib is a 2-aminoisobutyric acid residue;
Xaa, $Xaa^1$, and $Xaa^2$ are independently one or more natural or non-natural amino acids, essential amino acids, or non-essential amino acids, or amino acids having L or D configuration;

$Z^1$ and $Z^2$ are independently a targeting moiety, cargo moiety, or nothing, wherein at least one is a targeting moiety;

$Y^1$ and $Y^2$ are independently nothing or a linker, or a linker having a cargo moiety;

$X^1$ and $X^2$ are independently nothing, a coupling group, one or more beta-alanine residues, or a polypeptide; and n1 and n3 are independently an integer greater than 0 and less than or equal to 50;

n2 n4, n5, n6, and n7 are independently 0-50,

Formula $10=Z^1-Y^1-X^1-(Aib)_{n1}-(Xaa^1)_{n2}-(KP)_{n3}-(Xaa^2)_{n4}-X^2-Y^2-Z^2$;

Formula $11=Z^1-Y^1-X^1-(Aib)_{n1}-(Xaa^1)_{n2}-(KP)_{n3}-(Xaa^2)_{n4}$;

Formula $12=(Aib)_{n1}-(Xaa^1)_{n2}-(KP)_{n3}-(Xaa^2)_{n4}-X^2-Y^2-Z^2$;

Formula $10A=Z^1-Y^1-X^1-(Aib)_{n1}-(Xaa^1)_{n2}-(KP)_{n3}-(Xaa^2)_{n4}-(KP1)_{n5}-X^2-Y^2-Z^2$;

Formula $11A=Z^1-Y^1-X^1-(Aib)_{n1}-(Xaa^1)_{n2}-(KP)_{n3}-(Xaa^2)_{n4}-(KP1)_{n5}$;

Formula $12A=(Aib)_{n1}-(Xaa^1)_{n2}-(KP)_{n3}-(Xaa^2)_{n4}-(KP1)_{n5}-X^2-Y^2-Z^2$;

Formula $10B=Z^1-Y^1-X^1-(Aib)_{n1}-(Xaa^1)_{n2}-(KP)_{n3}-(Xaa^2)_{n4}-(KP1)_{n5}-(Xaa^3)_{n6}-X^2-Y^2-Z^2$;

Formula $11B=Z^1-Y^1-X^1-(Aib)_{n1}-(Xaa^1)_{n2}-(KP)_{n3}-(Xaa^2)_{n4}-(KP1)_{n5}-(Xaa^3)_{n6}$;

Formula $12B=(Aib)_{n1}-(Xaa^1)_{n2}-(KP)_{n3}-(Xaa^2)_{n4}-(KP1)_{n5}-(Xaa^3)_{n6}-X^2-Y^2-Z^2$;

Formula $10C=Z^1-Y^1-X^1-(Xaa^4)_{n7}-(Aib)_{n1}-(Xaa^1)_{n2}-(KP)_{n3}-(Xaa^2)_{n4}-(KP1)_{n5}-X^2-Y^2-Z^2$;

Formula $11C=Z^1-Y^1-X^1-(Xaa^4)_{n7}-(Aib)_{n1}-(Xaa^1)_{n2}-(KP)_{n3}-(Xaa^2)_{n4}-(KP1)_{n5}$; and Formula $12C=(Xaa^4)_{n7}-(Aib)_{n1}-(Xaa^1)_{n2}-(KP)_{n3}-(Xaa^2)_{n4}-(KP1)_{n5}-X^2-Y^2-Z^2$.

7. The cell-targeting compound of claim 6, wherein the targeting moiety is on the C-terminus or on N-terminus.

8. The cell-targeting compound of claim 6, wherein $Z^1$ and $Z^2$ are independently a targeting moiety or cargo moiety, wherein at least one is a targeting moiety.

9. The cell-targeting compound of claim 6, wherein $Y^1$ and $Y^2$ are each a linker.

10. The cell-targeting compound of claim 6, $X^1$ and $X^2$ are each independently one or more beta-alanine residues.

11. The cell-targeting compound of claim 6, wherein $Y^1$ and $Y^2$ are each a linker and $X^1$ and $X^2$ are each independently one or more beta-alanine residues.

12. The cell-targeting compound of claim 11, wherein $Y^1$ and $Y^2$ are each a linker that includes one or more natural or non-natural amino acids, essential amino acids, or non-essential amino acids, or amino acids having L or D configuration or peptide thereof.

13. The cell-targeting compound of claim 6, wherein: $X^1-(Aib)_{n1}-(Xaa^1)_{n2}-(KP)_{n3}-(Xaa^2)_{n4}$ includes one of SEQ ID NOs: 9-38, 41-54 or 61-69.

14. The cell-targeting compound of claim 6, wherein n1 is 4.

15. The cell-targeting compound of claim 1, further comprising:
a cargo moiety linked to the peptide.

16. The cell-targeting compound of claim of claim 15, comprising the cargo moiety linked at an internal portion of the cell-targeting compound between the targeting moiety and the peptide.

17. The cell-targeting compound of claim 15, wherein the cargo moiety is a therapeutic agent, pharmaceutical, nutraceutical, diagnostic agent, assay agent, tracking agent, suicide agent, toxin, or any other agent.

18. A cell-targeting compound comprising one of SEQ ID NOs: 5-38, 40-54 or 61-69 comprising:
one of Formulae 10-10C, 11-11C, or 12-12C wherein:
KP and KP1 are independently one or more amino acids independently selected from proline and glycine that can cause the endosomal-disrupting kinked peptide to kink;
Aib is a 2-aminoisobutyric acid residue;
Xaa, $Xaa^1$, and $Xaa^2$ are independently one or more natural or non-natural amino acids, essential amino acids, or non-essential amino acids, or amino acids having L or D configuration;
$Z^1$ and $Z^2$ are independently a targeting moiety, cargo moiety, or nothing, wherein at least one is a targeting moiety;
$Y^1$ and $Y^2$ are independently nothing or a linker, or a linker having a cargo moiety;
$X^1$ and $X^2$ are independently nothing, a coupling group, one or more beta-alanine residues, or a polypeptide; and
n1 is an integer greater than or equal to 2 and less than or equal to 50;
n3 is an integer greater than 0 and less than or equal to 50;
n2 n4, n5, n6, and n7 are independently 0-50, Formula $10=Z^1-Y^1-X^1-(Aib)_{n1}-(Xaa^1)_{n1}-(KP)_{n3}-(Xaa^2)_{n4}-X^2-Y^2-Z^2$;

Formula $11=Z^1-Y^1-X^1-(Aib_{n1}-(Xaa^1)_{n2}-(KP)_{n3}-(Xaa^2)_{n4}$;

Formula $12=(Aib)_{n1}-(Xaa^1)_{n2}-(KP)_{n3}-(Xaa^2)_{n4}-X^2-Y^2-Z^2$;

Formula $10A=Z^1-Y^1-X^1-(Aib)_{n1}-(Xaa^1)_{n2}-(KP)_{n3}-(Xaa^2)_{n4}-(KP1)_{n5}-X^2-Y^2-Z^2$;

Formula $11A=Z^1-Y^1-X^1-(Aib)_{n1}-(Xaa^1)_{n2}-(KP)_{n3}-(Xaa^2)_{n4}-(KP1)_{n5}$;

Formula $12A=(Aib)_{n1}-(Xaa^1)_{n2}-(KP)_{n3}-(Xaa^2)_{n4}-(KP1)_{n5}-X^2-Y^2-Z^2$;

Formula $10B=Z^1-Y^1-X^1-(Aib)_{n1}-(Xaa^1)_{n2}-(KP)_{n3}-(Xaa^2)_{n4}-(KP1)_{n5}-(Xaa^3)_{n6}-X^2-Y^2-Z^2$;

Formula $11B=Z^1-Y^1-X^1-(Aib)_{n1}-(Xaa^1)_{n2}-(KP)_{n3}-(Xaa^2)_{n4}-(KP1)_{n5}-(Xaa^3)_{n6}$;

Formula $12B=(Aib)_{n1}-(Xaa^1)_{n2}-(KP)_{n3}-(Xaa^2)_{n4}-(KP1)_{n5}-(Xaa^3)_{n6}-X^2-Y^2-Z^2$;

Formula $10C=Z^1-Y^1-X^1-(Xaa^4)_{n7}-(Aib)_{n1}-(Xaa^1)_{n2}-(KP)_{n3}-(Xaa^2)_{n4}-(KP1)_{n5}-X^2-Y^2-Z^2$;

Formula $11C=Z^1-Y^1-X^1-(Xaa^4)_{n7}-(Aib)_{n1}-(Xaa^1)_{n2}-(KP)_{n3}-(Xaa^2)_{n4}-(KP1)_{n5}$; and Formula $12C=(Xaa^4)_{n7}-(Aib)_{n1}-(Xaa^1)_{n2}-(KP)_{n3}-(Xaa^2)_{n4}-(KP1)_{n5}-X^2-Y^2-Z^2$.

19. The cell-targeting compound of claim 18, wherein n1 is at least 4.

20. The cell-targeting compound of claim 18, wherein n1 is 3, 4, 5, 6, 7, 8, 1, 10, 15, 20, 25, 30, 35, 15, 45 or 50.

* * * * *

SEQUENCE LISTING

```
<160> NUMBER OF SEQ ID NOS: 77

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<223> OTHER INFORMATION: C-term CONH2

<400> SEQUENCE: 1

Glu Glu Xaa Xaa Ser Ser Ala Trp Trp Ser Tyr Trp Pro Pro Val Ala
1               5                   10                  15

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(4)
<223> OTHER INFORMATION: Aib

<400> SEQUENCE: 2

Xaa Xaa Xaa Xaa
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Tyr Ala Tyr Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp Trp Ala Tyr Trp
1               5

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<223> OTHER INFORMATION: C-term CONH2

<400> SEQUENCE: 5

Glu Glu Xaa Xaa Ala Ala Ala Trp Trp Ala Tyr Trp Pro Pro Val Ala
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon-Ahx amino acid or reaction product or derivative thereof,
``` which can be considered a nonstandard amino acid
<220> FEATURE:
<223> OTHER INFORMATION: C-term CONH2

<400> SEQUENCE: 6

Xaa Glu Glu Xaa Ser Ser Ala Trp Trp Ser Tyr Trp Pro Pro Val Ala
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<223> OTHER INFORMATION: C-term CONH2

<400> SEQUENCE: 7

Xaa Glu Glu Xaa Ala Ala Ala Trp Trp Ala Tyr Trp Pro Pro Val Ala
1               5                   10                  15

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<223> OTHER INFORMATION: C-term CONH2

<400> SEQUENCE: 8

Xaa Glu Glu Xaa Xaa Ala Ala Ala Trp Trp Ala Tyr Trp Pro Pro Val
1               5                   10                  15

Ala

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or reaction product or derivative thereof, which can be considered
a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 9

Xaa Glu Glu Xaa Xaa Xaa Xaa Trp Trp Ala Tyr Trp Pro Pro Val Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<221> NAME/KEY: MOD_RES
<222> LOCATION: (5)..(6)
<223> OTHER INFORMATION: 2-amino-2-methylpropanamide or
      2-amino-2-methylpropanoic acid or 2-aminoisobutyric acid or
      Aib amino acid or
      reaction product or derivative thereof, which can be
      considered a nonstandard amino acid
<220> FEATURE:
<223> OTHER INFORMATION: C-term CONH2

<400> SEQUENCE: 10

Xaa Glu Glu Xaa Xaa Xaa Trp Trp Ala Tyr Trp Pro Pro Val Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid -continued

```
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 11

Xaa Glu Glu Xaa Xaa Xaa Xaa Trp Trp Ala Tyr Trp Pro Pro Val
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid
      or reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 12

Xaa Glu Glu Xaa Xaa Xaa Xaa Ala Trp Ala Tyr Trp Pro Pro Val Ala
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2
```

<400> SEQUENCE: 13

Xaa Glu Glu Xaa Xaa Xaa Xaa Trp Ala Ala Tyr Trp Pro Pro Val Ala
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 14

Xaa Glu Glu Xaa Xaa Xaa Xaa Trp Trp Ala Ala Trp Pro Pro Val Ala
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 15

Xaa Glu Glu Xaa Xaa Xaa Xaa Trp Trp Ala Tyr Ala Pro Pro Val Ala
1               5                   10                  15

<210> SEQ ID NO 16
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 16

Xaa Glu Glu Xaa Xaa Xaa Xaa Trp Trp Ala Tyr Trp Ala Pro Val Ala
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or 2-amino-2-
      methylpropanoic acid or 2-aminoisobutyric acid or Aib amino acid
      or reaction product or derivative thereof, which can be
      considered a nonstandard amino acid
<220> FEATURE:
<223> OTHER INFORMATION: C-term CONH2

<400> SEQUENCE: 17

Xaa Glu Glu Xaa Xaa Xaa Xaa Trp Trp Ala Tyr Trp Pro Ala Val Ala
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
``` reaction product or derivative thereof, which can be considered
a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 18

Xaa Glu Glu Xaa Xaa Xaa Xaa Trp Trp Ala Tyr Trp Pro Pro Ala Ala
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<221> NAME/KEY: MOD_RES
<222> LOCATION: (5)..(7)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 19

Xaa Glu Glu Xaa Xaa Xaa Xaa Trp Trp Ala Trp Trp Pro Pro Val Ala
1               5                   10                  15

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid
      or reaction product or derivative thereof, which can be considered
      a nonstandard amino acid
<220> FEATURE:
<221> NAME/KEY: MOD_RES
<222> LOCATION: (4)..(4)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:

<221> NAME/KEY: MOD_RES
<222> LOCATION: (5)..(8)
<223> OTHER INFORMATION: 2-amino-2-methylpropanamide or
     2-amino-2-methylpropanoic acid or 2-aminoisobutyric acid or Aib
     amino acid or reaction product or derivative thereof, which can be
     considered a nonstandard amino acid
<220> FEATURE:
<223> OTHER INFORMATION: C-term CONH2

<400> SEQUENCE: 20

Xaa Glu Glu Xaa Xaa Xaa Xaa Xaa Trp Trp Ala Tyr Trp Pro Pro Val
1               5                   10                  15

Ala

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<221> NAME/KEY: MOD_RES
<222> LOCATION: (1)..(1)
<223> OTHER INFORMATION: 3-aminopropanamide or 3-aminopropanoic acid or
     reaction product or derivative thereof, which can be considered
     a nonstandard amino acid
<220> FEATURE:
<221> NAME/KEY: MOD_RES
<222> LOCATION: (4)..(5)
<223> OTHER INFORMATION: 6-aminohexanamide or 6-aminohexanoic acid or
     Epsilon-Ahx amino acid or reaction product or derivative thereof,
     which can be considered a nonstandard amino acid
<220> FEATURE:
<221> NAME/KEY: MOD_RES
<222> LOCATION: (6)..(9)
<223> OTHER INFORMATION: 2-amino-2-methylpropanamide or
     2-amino-2-methylpropanoic acid or 2-aminoisobutyric acid or Aib
     amino acid or reaction product or derivative thereof, which can be
     considered a nonstandard amino acid
<220> FEATURE:
<223> OTHER INFORMATION: C-term CONH2

<400> SEQUENCE: 21

Xaa Glu Glu Xaa Xaa Xaa Xaa Xaa Xaa Trp Trp Ala Tyr Trp Pro Pro
1               5                   10                  15

Val Ala

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<221> NAME/KEY: MOD_RES
<222> LOCATION: (1)..(1)
<223> OTHER INFORMATION: 3-aminopropanamide or 3-aminopropanoic acid or
     reaction product or derivative thereof, which can be considered
     a nonstandard amino acid
<220> FEATURE:
<221> NAME/KEY: MOD_RES
<222> LOCATION: (4)..(5)
<223> OTHER INFORMATION: 6-aminohexanamide or 6-aminohexanoic acid or
     Epsilon-Ahx amino acid or reaction product or derivative thereof,
     which can be considered a nonstandard amino acid
<220> FEATURE:
<221> NAME/KEY: MOD_RES
<222> LOCATION: (6)..(9)
<223> OTHER INFORMATION: 2-amino-2-methylpropanamide or
     2-amino-2-methylpropanoic acid or 2-aminoisobutyric acid or Aib
     amino acid or reaction product or derivative thereof, which can be

```
            considered a nonstandard amino acid
<220> FEATURE:
<223> OTHER INFORMATION: C-term CONH2

<400> SEQUENCE: 22

Xaa Glu Glu Xaa Xaa Xaa Xaa Xaa Xaa Phe Phe Ala Phe Phe Pro Pro
1               5                   10                  15

Val Ala

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 23

Xaa Glu Glu Xaa Xaa Xaa Xaa Xaa Xaa Tyr Tyr Ala Tyr Tyr Pro Pro
1               5                   10                  15

Val Ala

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 24
```

```
Xaa Glu Glu Xaa Xaa Xaa Xaa Xaa Xaa Tyr Tyr Tyr Tyr Tyr Pro Pro
1               5                   10                  15

Val Ala

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION: 6-aminohexanamide or 6-aminohexanoic acid or
      Epsilon-Ahx amino acid or reaction product or derivative thereof,
      which can be considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 25

Xaa Glu Glu Xaa Xaa Xaa Xaa Xaa Xaa Tyr Tyr Ala Tyr Tyr Pro Pro
1               5                   10                  15

Val Val

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can
      be considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 26

Xaa Glu Glu Xaa Xaa Xaa Xaa Xaa Xaa Trp Trp Ala Tyr Trp Pro Pro
1               5                   10                  15
```

Val Ala

```
<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can
      be considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 27

Xaa Glu Glu Xaa Xaa Xaa Xaa Xaa Xaa Trp Trp Ala Tyr Trp Pro Pro
1               5                   10                  15

Val Ala Ala

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can
      be considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 28

Xaa Glu Glu Xaa Xaa Xaa Xaa Xaa Xaa Tyr Tyr Ala Tyr Tyr Pro Pro
1               5                   10                  15
```

-continued

Val Val

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can be
      considered a nonstandard amino acid
<220> FEATURE:
<221> NAME/KEY: MOD_RES
<222> LOCATION: (6)..(9)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 29

Xaa Glu Glu Xaa Xaa Xaa Xaa Xaa Xaa Tyr Tyr Tyr Tyr Tyr Pro Pro
1               5                   10                  15

Val Val

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: (S)-2-aminopent-4-ynamide or
      (S)-2-aminopent-4-ynanoic acid or vinylglycine or reaction product
      or derivative thereof, which can be considered a nonstandard
      amino acid
<220> FEATURE:
<221> NAME/KEY: MOD_RES
<222> LOCATION: (5)..(6)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can
      be considered a nonstandard amino acid
<220> FEATURE:
<221> NAME/KEY: MOD_RES
<222> LOCATION: (7)..(10)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

-continued

<400> SEQUENCE: 30

Xaa Glu Glu Xaa Xaa Xaa Xaa Xaa Xaa Xaa Tyr Tyr Ala Tyr Tyr Pro
1               5                   10                  15

Pro Val Val

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(4)
<223> OTHER INFORMATION: (S)-2-aminopent-4-ynamide or
      (S)-2-aminopent-4-ynanoic acid or vinylglycine or reaction product
      or derivative thereof, which can be considered a nonstandard amino
      acid
<220> FEATURE:
<221> NAME/KEY: MOD_RES
<222> LOCATION: (5)..(6)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can
      be considered a nonstandard amino acid
<220> FEATURE:
<221> NAME/KEY: MOD_RES
<222> LOCATION: (7)..(10)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 31

Xaa Glu Glu Xaa Xaa Xaa Xaa Xaa Xaa Xaa Trp Trp Ala Tyr Trp Pro
1               5                   10                  15

Pro Val Ala

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can
      be considered a nonstandard amino acid
<220> FEATURE:
<221> NAME/KEY: MOD_RES
<222> LOCATION: (6)..(9)

```
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 32

Xaa Glu Glu Xaa Xaa Xaa Xaa Xaa Xaa Trp Trp Ala Tyr Trp Pro Pro
1               5                   10                  15

Val Ala

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (2)..(2)
<223> OTHER INFORMATION: (S)-2-aminopent-4-ynamide or
      (S)-2-aminopent-4-ynanoic acid or vinylglycine or reaction product
      or derivative thereof, which can be considered a nonstandard amino
      acid
<220> FEATURE:
<221> NAME/KEY: MOD_RES
<222> LOCATION: (3)..(4)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can be
      considered a nonstandard amino acid
<220> FEATURE:
<221> NAME/KEY: MOD_RES
<222> LOCATION: (5)..(8)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 33

Xaa Xaa Xaa Xaa Xaa Xaa Xaa Xaa Trp Trp Ala Tyr Trp Pro Pro Val
1               5                   10                  15

Ala

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid or
      reaction product or derivative thereof, which can be considered
      a nonstandard amino acid
<220> FEATURE:
<221> NAME/KEY: MOD_RES
<222> LOCATION: (4)..(5)
<223> OTHER INFORMATION:
      3-(2-(2-(2-aminoethoxy)ethoxy)ethoxy)propanamide or
```

```
        3-(2-(2-(2-aminoethoxy)ethoxy)ethoxy)propanoic acid or mini-PEG
        amino acid or reaction product or derivative thereof, which can be
        considered a nonstandard amino acid
<220> FEATURE:
<221> NAME/KEY: MOD_RES
<222> LOCATION: (6)..(9)
<223> OTHER INFORMATION: 2-amino-2-methylpropanamide or
        2-amino-2-methylpropanoic acid or 2-aminoisobutyric acid or Aib
        amino acid or reaction product or derivative thereof, which can be
        considered a nonstandard amino acid
<220> FEATURE:
<223> OTHER INFORMATION: C-term CONH2

<400> SEQUENCE: 34

Xaa Glu Glu Xaa Xaa Xaa Xaa Xaa Xaa Trp Trp Ala Tyr Trp Pro Pro
1               5                   10                  15

Val Ala

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(1)
<223> OTHER INFORMATION: 3-aminopropanamide or 3-aminopropanoic acid or
        reaction product or derivative thereof, which can be considered
        a nonstandard amino acid
<220> FEATURE:
<221> NAME/KEY: MOD_RES
<222> LOCATION: (4)..(4)
<223> OTHER INFORMATION: (S)-2-aminopent-4-ynamide or
        (S)-2-aminopent-4-ynanoic acid or vinylglycine or reaction
        product or derivative thereof, which can be considered a
        nonstandard amino acid
<220> FEATURE:
<221> NAME/KEY: MOD_RES
<222> LOCATION: (5)..(6)
<223> OTHER INFORMATION:
        3-(2-(2-(2-aminoethoxy)ethoxy)ethoxy)propanamide or
        3-(2-(2-(2-aminoethoxy)ethoxy)ethoxy)propanoic acid or mini-PEG
        amino acid or reaction product or derivative thereof, which can
        be considered a nonstandard amino acid
<220> FEATURE:
<221> NAME/KEY: MOD_RES
<222> LOCATION: (7)..(10)
<223> OTHER INFORMATION: 2-amino-2-methylpropanamide or
        2-amino-2-methylpropanoic acid or 2-aminoisobutyric acid or Aib
        amino acid or reaction product or derivative thereof, which can be
        considered a nonstandard amino acid
<220> FEATURE:
<223> OTHER INFORMATION: C-term CONH2

<400> SEQUENCE: 35

Xaa Glu Glu Xaa Xaa Xaa Xaa Xaa Xaa Xaa Trp Trp Ala Tyr Trp Pro
1               5                   10                  15

Pro Val Ala

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(1)
<223> OTHER INFORMATION: 3-aminopropanamide or 3-aminopropanoic acid or
        reaction product or derivative thereof, which can be considered
``` a nonstandard amino acid
<220> FEATURE:
<221> NAME/KEY: MOD_RES
<222> LOCATION: (4)..(4)
<223> OTHER INFORMATION: (S)-2-aminopent-4-ynamide or
    (S)-2-aminopent-4-ynanoic acid or vinylglycine or reaction product
    or derivative thereof, which can be considered a nonstandard amino
    acid
<220> FEATURE:
<221> NAME/KEY: MOD_RES
<222> LOCATION: (5)..(6)
<223> OTHER INFORMATION:
    3-(2-(2-(2-aminoethoxy)ethoxy)ethoxy)propanamide or
    3-(2-(2-(2-aminoethoxy)ethoxy)ethoxy)propanoic acid or mini-PEG
    amino acid or reaction product or derivative thereof, which can be
    considered a nonstandard amino acid
<220> FEATURE:
<221> NAME/KEY: MOD_RES
<222> LOCATION: (7)..(10)
<223> OTHER INFORMATION: 2-amino-2-methylpropanamide or
    2-amino-2-methylpropanoic acid or 2-aminoisobutyric acid or Aib
    amino acid or reaction product or derivative thereof, which can be
    considered a nonstandard amino acid
<220> FEATURE:
<223> OTHER INFORMATION: C-term CONH2

<400> SEQUENCE: 36

Xaa Glu Glu Xaa Xaa Xaa Xaa Xaa Xaa Xaa Trp Trp Ala Tyr Trp Pro
1               5                   10                  15

Pro Val Val

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (1)..(1)
<223> OTHER INFORMATION: 3-aminopropanamide or 3-aminopropanoic acid or
    reaction product or derivative thereof, which can be considered
    a nonstandard amino acid
<220> FEATURE:
<221> NAME/KEY: MOD_RES
<222> LOCATION: (4)..(4)
<223> OTHER INFORMATION: (S)-2-aminopent-4-ynamide or
    (S)-2-aminopent-4-ynanoic acid or vinylglycine or reaction
    product or derivative thereof, which can be considered a
    nonstandard amino acid
<220> FEATURE:
<221> NAME/KEY: MOD_RES
<222> LOCATION: (5)..(6)
<223> OTHER INFORMATION:
    3-(2-(2-(2-aminoethoxy)ethoxy)ethoxy)propanamide or
    3-(2-(2-(2-aminoethoxy)ethoxy)ethoxy)propanoic acid
    or mini-PEG amino acid or reaction product or derivative
    thereof, which can be considered a nonstandard amino acid
<220> FEATURE:
<221> NAME/KEY: MOD_RES
<222> LOCATION: (7)..(10)
<223> OTHER INFORMATION: 2-amino-2-methylpropanamide or
    2-amino-2-methylpropanoic acid or 2-aminoisobutyric acid or Aib
    amino acid or reaction product or derivative thereof, which can be
    considered a nonstandard amino acid
<220> FEATURE:
<223> OTHER INFORMATION: C-term CONH2

<400> SEQUENCE: 37

Xaa Glu Glu Xaa Xaa Xaa Xaa Xaa Xaa Xaa Trp Trp Ala Tyr Tyr Pro
1               5                   10                  15

Pro Val Val

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminopropanamide or 3-aminopropanoic acid
      or reaction product or derivative thereof, which can be considered
      a nonstandard amino acid
<220> FEATURE:
<221> NAME/KEY: MOD_RES
<222> LOCATION: (4)..(4)
<223> OTHER INFORMATION: (S)-2-aminopent-4-ynamide or
      (S)-2-aminopent-4-ynanoic acid or vinylglycine or reaction product
      or derivative thereof, which can be considered a nonstandard
      amino acid
<220> FEATURE:
<221> NAME/KEY: MOD_RES
<222> LOCATION: (5)..(6)
<223> OTHER INFORMATION:
      3-(2-(2-(2-aminoethoxy)ethoxy)ethoxy)propanamide or
      3-(2-(2-(2-aminoethoxy)ethoxy)ethoxy)propanoic acid or mini-PEG
      amino acid or reaction product or derivative thereof, which can be
      considered a nonstandard amino acid
<220> FEATURE:
<221> NAME/KEY: MOD_RES
<222> LOCATION: (7)..(10)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 38

Xaa Glu Glu Xaa Xaa Xaa Xaa Xaa Xaa Xaa Tyr Tyr Ala Tyr Tyr Pro
1               5                   10                  15

Pro Val Val

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 39

Ser Ser Ala Trp Trp Ser Tyr Trp Pro Pro Val Ala
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 40

```
Ala Ala Ala Trp Trp Ala Tyr Trp Pro Pro Val Ala
1               5                   10
```

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(3)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 41

```
Xaa Xaa Xaa Trp Trp Ala Tyr Trp Pro Pro Val Ala
1               5                   10
```

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 42

```
Xaa Xaa Xaa Xaa Trp Trp Ala Tyr Trp Pro Pro Val Ala
1               5                   10
```

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 43

```
Xaa Xaa Xaa Xaa Trp Trp Ala Tyr Trp Pro Pro Val Ala
1               5                   10
```

```
<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 44

Xaa Xaa Xaa Xaa Trp Trp Ala Tyr Trp Pro Pro Val Val
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 45

Xaa Xaa Xaa Xaa Ala Trp Ala Tyr Trp Pro Pro Val Val
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 46

Xaa Xaa Xaa Xaa Trp Ala Ala Tyr Trp Pro Pro Val Val
1               5                   10

<210> SEQ ID NO 47
<211> LENGTH: 13
<212> TYPE: PRT
<213> ORGANISM: Artificial Sequence
```

<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 47

Xaa Xaa Xaa Xaa Trp Trp Ala Ala Trp Pro Pro Val Val
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 48

Xaa Xaa Xaa Xaa Trp Trp Ala Tyr Ala Pro Pro Val Val
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 49

Xaa Xaa Xaa Xaa Trp Trp Ala Tyr Trp Ala Pro Val Val
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 50

Xaa Xaa Xaa Xaa Trp Trp Ala Tyr Trp Pro Ala Val Val
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 51

Xaa Xaa Xaa Xaa Trp Trp Ala Tyr Trp Pro Pro Ala Val
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 52

Xaa Xaa Xaa Xaa Tyr Trp Ala Trp Trp Pro Pro Val Val
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
```

```
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 53

Xaa Xaa Xaa Xaa Trp Tyr Ala Trp Trp Pro Pro Val Val
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3N+
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 54

Xaa Xaa Xaa Xaa Trp Trp Ala Trp Tyr Pro Pro Val Val
1               5                   10

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000
```

```
<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(5)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 61

Xaa Xaa Xaa Xaa Xaa Trp Trp Ala Tyr Trp Pro Pro Val Ala
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 62

Xaa Xaa Xaa Xaa Tyr Tyr Ala Tyr Tyr Pro Pro Val Val
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 63

Xaa Xaa Xaa Xaa Trp Trp Ala Tyr Trp Pro Pro Val Val
1               5                   10

<210> SEQ ID NO 64
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 64

Xaa Xaa Xaa Xaa His His Ala His His Pro Pro Val Val
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 65

Xaa Xaa Xaa Xaa Trp Trp Ala Tyr Trp Pro Pro Val Leu
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 66

Xaa Xaa Xaa Xaa Trp Trp Ala Tyr Trp Pro Pro Leu Val
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 67

Xaa Xaa Xaa Xaa Trp Trp Ala Tyr Trp Pro Pro Leu Leu
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 68

Xaa Xaa Xaa Xaa Trp Trp Gly Tyr Trp Pro Pro Val Ala
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(4)
<223> OTHER INFORMATION: 2-amino-2-methylpropanamide or
      2-amino-2-methylpropanoic acid or 2-aminoisobutyric acid or Aib
      amino acid or reaction product or derivative thereof, which can be
      considered a nonstandard amino acid
<220> FEATURE:
<223> OTHER INFORMATION: C-term CONH2

<400> SEQUENCE: 69

Xaa Xaa Xaa Xaa Tyr Tyr Ala Tyr Tyr Pro Pro Val Val
1               5                   10

<210> SEQ ID NO 70

<400> SEQUENCE: 70
```

```
000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
guacggaaua gauaauuaau t                                              21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
uuaauuaucu auuccguacu u                                              21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
guacggaaua gauaauuaau u                                              21
```